(12) United States Patent
Bhalla et al.

(10) Patent No.: US 11,293,920 B2
(45) Date of Patent: Apr. 5, 2022

(54) NANOPLASMONIC INSTRUMENTATION, MATERIALS, METHODS AND SYSTEM INTEGRATION

(71) Applicant: OKINAWA INSTITUTE OF SCIENCE AND TECHNOLOGY SCHOOL CORPORATION, Okinawa (JP)

(72) Inventors: Nikhil Bhalla, Okinawa (JP); Amy Shen Fried, Okinawa (JP); Kang-Yu Chu, Okinawa (JP)

(73) Assignee: OKINAWA INSTITUTE OF SCIENCE AND TECHNOLOGY SCHOOL CORPORATION, Okinawa (JP)

(*) Notice: Subject to any disclaimer, the term of this patent is extended or adjusted under 35 U.S.C. 154(b) by 202 days.

(21) Appl. No.: 16/606,037

(22) PCT Filed: Apr. 18, 2018

(86) PCT No.: PCT/JP2018/016893
§ 371 (c)(1),
(2) Date: Oct. 17, 2019

(87) PCT Pub. No.: WO2018/194184
PCT Pub. Date: Oct. 25, 2018

(65) Prior Publication Data
US 2021/0140954 A1    May 13, 2021

Related U.S. Application Data

(60) Provisional application No. 62/486,877, filed on Apr. 18, 2017.

(51) Int. Cl.
*G01N 21/75* (2006.01)
*G01N 33/543* (2006.01)
(Continued)

(52) U.S. Cl.
CPC ....... *G01N 33/54373* (2013.01); *C03C 17/09* (2013.01); *G01N 21/554* (2013.01);
(Continued)

(58) Field of Classification Search
CPC .. G01N 21/658; G01N 21/554; G01N 21/648; G01N 21/41; G01N 2021/651;
(Continued)

(56) References Cited

U.S. PATENT DOCUMENTS 9,567,214 B2 * 2/2017 Zhou ................. G01N 21/554
2011/0128536 A1   6/2011 Bond et al.
(Continued)

FOREIGN PATENT DOCUMENTS

| JP | 2007-101308 A | | 4/2007 |
|---|---|---|---|
| KR | 20140140886 A | * | 12/2014 |
| KR | 1020130061862 | * | 1/2016 |

OTHER PUBLICATIONS

Li, Wen-Di et al, "Extraordinary light transmission through opaque thin metal film with subwavelength holes blocked by metal disks", Optics Express, vol. 19, No. 21, Oct. 7, 2011, pp. 21098-21108; Cited in Extended European Search Report dated Mar. 12, 2020. (11 pages).
(Continued)

*Primary Examiner* — Hoa Q Pham
(74) *Attorney, Agent, or Firm* — WHDA, LLP

(57) ABSTRACT

A method for making a plasmonic mushroom array includes: forming a plurality of metal nano-islands each having nanometer-range dimensions on a surface of a glass substrate; and subjecting to the glass substrate having the plurality of metal nano-islands formed thereon to reactive ion etching such that the plurality of metal nano-islands are converted to a plurality of mushroom-shaped structures each having a metal cap supported by a pillar made of a material of the
(Continued)

glass substrate and each having dimensions smaller than the dimensions of the nano-islands, the plurality of mushroom-shaped structures being arranged in a substantially regular pattern with intervals smaller than average intervals between the nano-islands, thereby forming the plurality of nano-scale mushroom-shaped structures on the glass substrate that can exhibit localized surface plasmon resonance.

16 Claims, 49 Drawing Sheets

(51) Int. Cl.
  C03C 17/09 (2006.01)
  G01N 21/552 (2014.01)
  G01N 21/41 (2006.01)
(52) U.S. Cl.
  CPC .. C03C 2217/255 (2013.01); C03C 2218/151 (2013.01); C03C 2218/33 (2013.01); G01N 21/41 (2013.01)
(58) Field of Classification Search
  CPC ......... G01N 27/3278; G01N 33/54346; G01N 33/587; H01L 29/0665; B82Y 15/0665; C23C 14/16; B01L 7/52; C03C 17/09
  USPC .................................. 356/301–326, 445–448
  See application file for complete search history.

(56) References Cited

U.S. PATENT DOCUMENTS

| | | | |
|---|---|---|---|
| 2012/0062884 A1* | 3/2012 | Sakagami | G01J 3/44 356/301 |
| 2014/0011013 A1 | 1/2014 | Jin et al. | |
| 2014/0045209 A1 | 2/2014 | Chou et al. | |
| 2014/0154668 A1 | 6/2014 | Chou et al. | |
| 2016/0169886 A1 | 6/2016 | Chou | |
| 2016/0223467 A1 | 8/2016 | Suh et al. | |
| 2019/0310200 A1* | 10/2019 | Lee | G01N 21/65 |
| 2021/0205816 A1* | 7/2021 | Jeong | B01L 7/52 |

OTHER PUBLICATIONS

Li, Wen-Di et al, "Three-dimensional cavity nanoantenna coupled plasmonic nanodots for ultrahigh and uniform surface-enhanced Raman scattering over large area", Optics Express, vol. 19, No. 5, Feb. 14, 2011, pp. 3925-3936; Cited in Extended European Search Report dated Mar. 12, 2020. (12 pages).
Choi, C.J. et al., "SERS sensors for biomedical tubing", Procedia Engineering, vol. 25, Nov. 4, 2011, pp. 76-79; Cited in Extended European Search Report dated Mar. 12, 2020. (4 pages).
Ahn, Myeong-Su et al., "Complementary Plasmonic Structures of Nanohole and Nanodisk Arrays with High Angular Sensitivity", 2016 International Conference on Optical Mems and Nanophotonics, Jan. 1, 2016; Cited in Extended European Search Report dated Mar. 12, 2020. (2 pages).
Extended (Supplementary) European Search Report dated Mar. 12, 2020, issued in counterpart EP Application No. 187887434.1. (20 pages).
Ostrikov, K., "Colloquium: Reactive Plasmas as a Versatile Nanofabrication Tool.", Reviews of Modem Physics, 2005, vol. 77, No. 2, pp. 489-511; Cited in Specification. (23 pages).
Vladimirov, S. V. et al., "Physics and Applications of Complex Plasmas", World Scientific, 2005; Cited in Specification. (4 pages).
Ostrikov,K. "Plasma Nanoscience: From Nature's Mastery to Deterministic Plasma-Aided Nanofabrication.", IEEE Transactions on Plasma Science, 2007, vol. 35, No. 2, pp. 127-136; Cited in Specification. (10 pages).

Hammond, J. L. et al., "Localized Surface Plasmon Resonance as a Biosensing Platform for Developing Countries.", Biosensors, 2014, vol. 4, No. 2, pp. 172-188; Cited in Specification and ISR dated Jun. 19, 2018. (17 pages).
Anker, J. N. et al., "Biosensing with Plasmonic Nanosensors." Nature Materials, 2008, vol. 7, No. 6, pp. 442-453; Cited in Specification. (13 pages).
Willets, K, A. et al., "Localized Surface Plasmon Resonance Spectroscopy and Sensing." Annu. Rev. Phys. Chem., 2007, vol. 58, pp. 267-297; Cited in Specification. (33 pages).
Kang, T, Y. et al., "Process Optimization of CF 4/Ar Plasma Etching of Au Using I-Optimal Design." Thin Solid Films, 2009, vol. 517, No. 14, pp. 3919-3922; Cited in Specification and ISR dated Jun. 19, 2018. (4 pages).
Knizikevicius, R., "Simulations of Si and SiO2 etching in SF6+ O2 plasma ", Vacuum, 2009, vol. 83, No. 6, pp. 953-957; Cited in Specification. (6 pages).
Jia, K. et al., "Sensitive Localized Surface Plasmon Resonance Multiplexing Protocols.", Analytical Chemistry, 2012, vol. 84, No. 18, pp. 8020-8027; Cited in Specification and ISR dated Jun. 19, 2018. (8 pages).
Svorcik, V. et al., "Annealing of Gold Nanostructures Sputtered on Glass Substrate ", Applied Physics A, 2011, vol. 102No. 3, pp. 605-610; Cited in Specification and ISR dated Jun. 19, 2018. (7 pages).
Manzano, M. et al., "Development of Localized Surface Plasmon Resonance Biosensors for the Detection of Brettanomyces Bruxellensis in Wine." Sensors and Actuators B: Chemical, 2016, vol. 223, pp. 295-300; Cited in Specification and ISR dated Jun. 19, 2018. (6 pages).
Ou, Y. et al., "Broadband Antireflection Silicon Carbide Surface by Self-assembled Nanopatterned Reactive-ion Etching.", Optical Materials Express 2013, vol. 3, No. 1, pp. 86-94; Cited in Specification. (9 pages).
Kitabayashi, H. et al., "Charging of Glass Substrate by Plasma Exposure", Japanese Journal of Applied Physics, May 1999, vol. 38, Part 1, No. 5A, pp. 2964-2968; Cited in Specification. (6 pages).
Becker, J. et al., "The Optimal Aspect Ratio of Gold Nanorods for Plasmonic Bio-sensing" Plasmonics, 2010, vol. 5, pp. 161-167; Cited in Specification. (8 pages).
Paivanranta, B. et al., "High Aspect Ratio Plasmonic Nanostructures for Sensing Applications", ACS Nano, 2011, vol. 5, No. 8, pp. 6374-6382; Cited in Specification. (9 pages).
Parsons, J. et al. "Localized Surface-plasmon Resonances in Periodic Nondiffracting Metallic Nanoparticle and Nanohole Arrays", Physical Review B, Feb. 2009, vol. 79, pp. 073412; Cited in Specification. (5 pages).
Abbas, A. et al., "Hot Spot-localized Artificial Antibodies for Label-free Plasmonic Biosensing" Advanced functional materials, Apr. 2013, vol. 23, pp. 1789-1797; Cited in Specification. (18 pages).
Sepu'lveda, B. et al., "Lspr-based Nanobiosensors" Nano Today, 2009, vol. 4, pp. 244-251; Cited in Specification. (8 pages).
Wilkinson, C. et al., "The Use of Materials Patterned on a Nano-and Micro-metric scale in Cellular Engineering", Materials Science and Engineering: C, 2002, vol. 19, pp. 263-269 Cited in Specification. (7 pages).
Armbruster, D. A. et al., "Limit of blank, limit of detection and limit of quantitation", Clin Biochem Rev., Aug. 2008, vol. 29, pp. S49-S52; Cited in Specification. (5 pages).
Sueyoshi, H. et al., "Microwave Heating of Thin Au Film", Material Transactions, Feb. 2007, vol. 48, No. 3, pp. 531-537; Cited in the ISR dated Jun. 19, 2018. (7 pages).
Bhalla, N. et al., "Plasma-assisted Large-Scale Nanoassembly of Metal-insulator Bioplasmonic Mushrooms", Applied Material and Interfaces, Dec. 13, 2017, vol. 10, pp. 219-226; Cited in the ISR dated Jun. 19, 2018. (8 pages).
Bhalla, N. et al., "Large-Scale Nanophotonic Structure for Long-term monitoring of Cell Proliferation", Advanced Biosystems, Jan. 19, 2018, vol. 2, 1700258; Cited in the ISR dated Jun. 19, 2018. (7 pages).

(56) References Cited

OTHER PUBLICATIONS

Garifullina, A. et al., "Probing Specific Gravity in Real-time with Graphene Oxide Plasmonics", Analytical Methods, Dec. 6, 2017, vol. 10, pp. 290-297; Cited in the ISR dated Jun. 19, 2018. (8 pages).
International Search Report dated Jun. 19, 2018, issued in counterpart JP Application No. PCT/JP2018/016893. (3 pages).
Office Action dated Sep. 14, 2021, issued in counterpart Japanese Application No. 2019-555708 (w/ English translation; 9 pages).
Office Action dated Feb. 22, 2022, issued in counterpart Japanese Application No. 2019-555708 (15 pages; w/ English translation).

\* cited by examiner

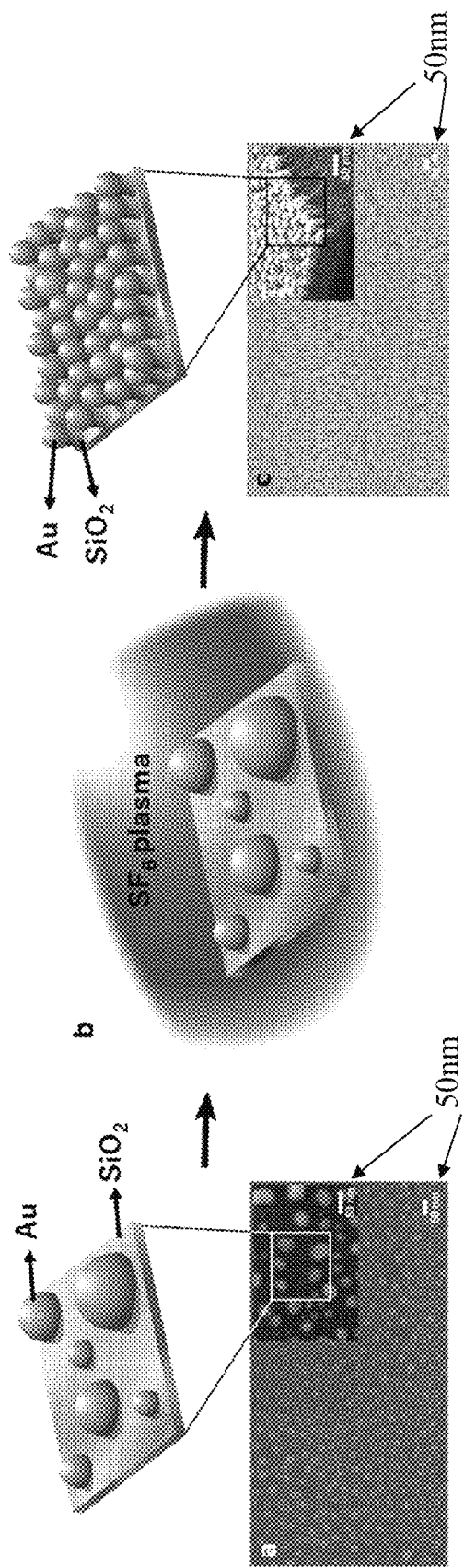
[FIG. 1]

[FIG. 2]
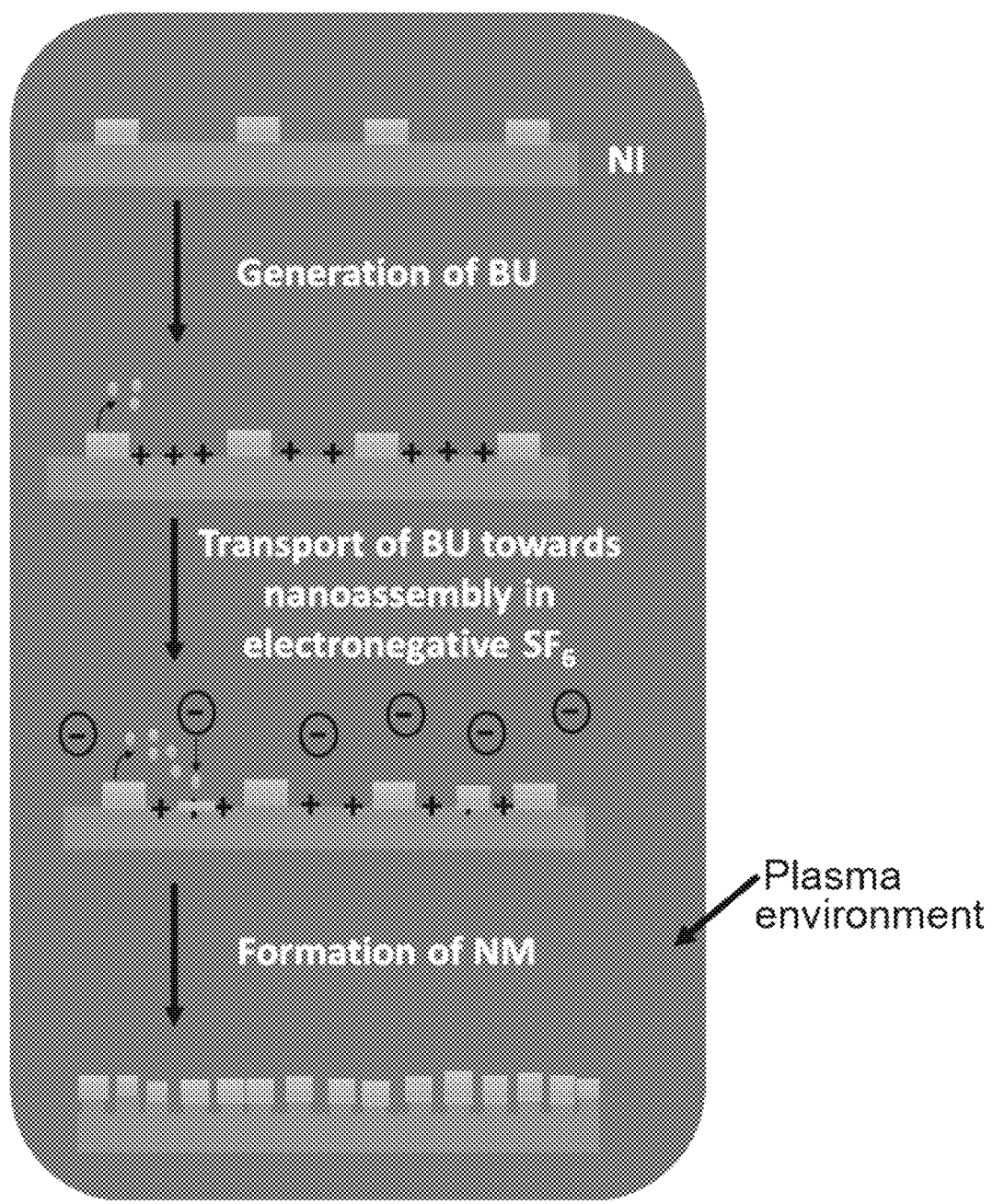

[FIG. 3]
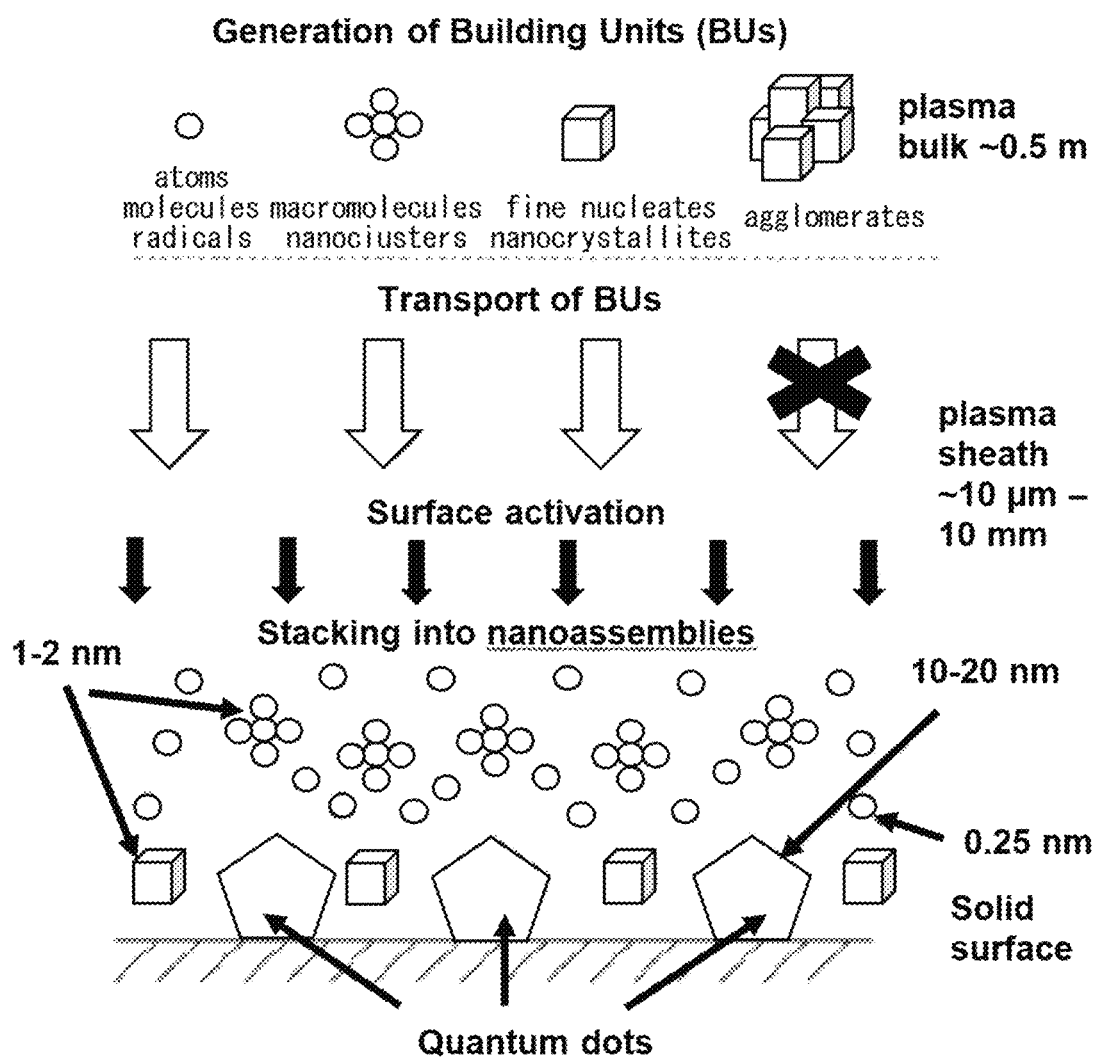

[FIG. 4]
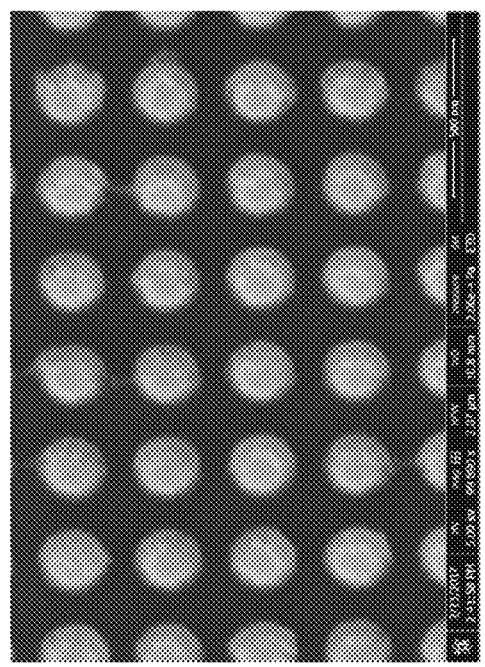

[FIG. 5]
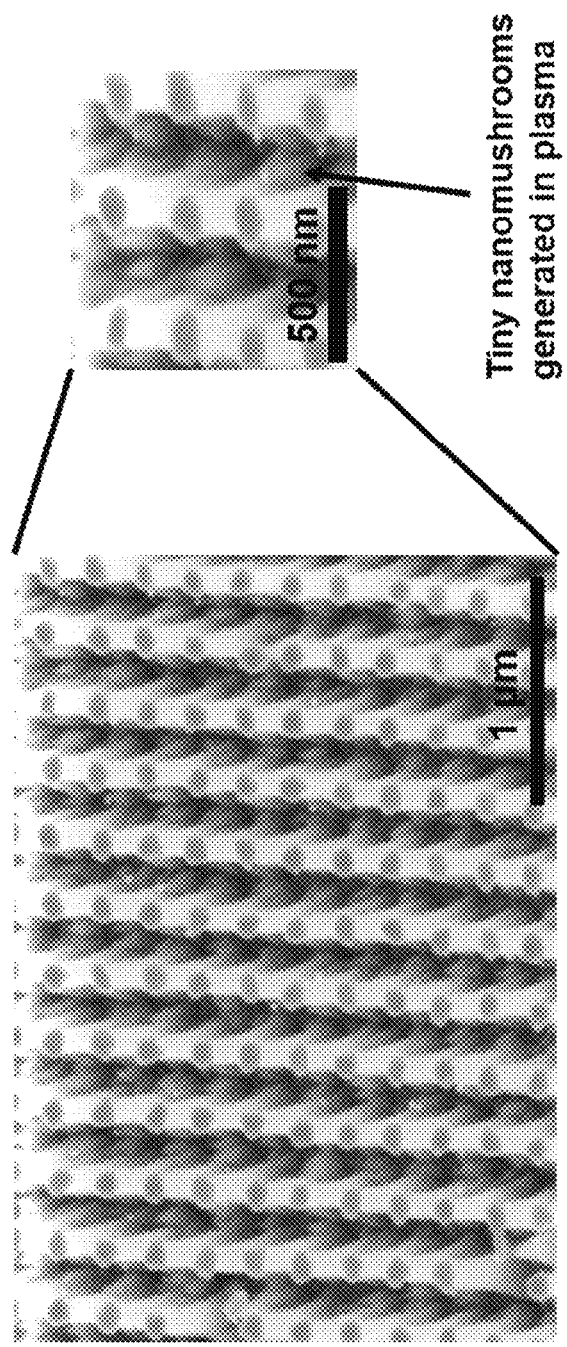

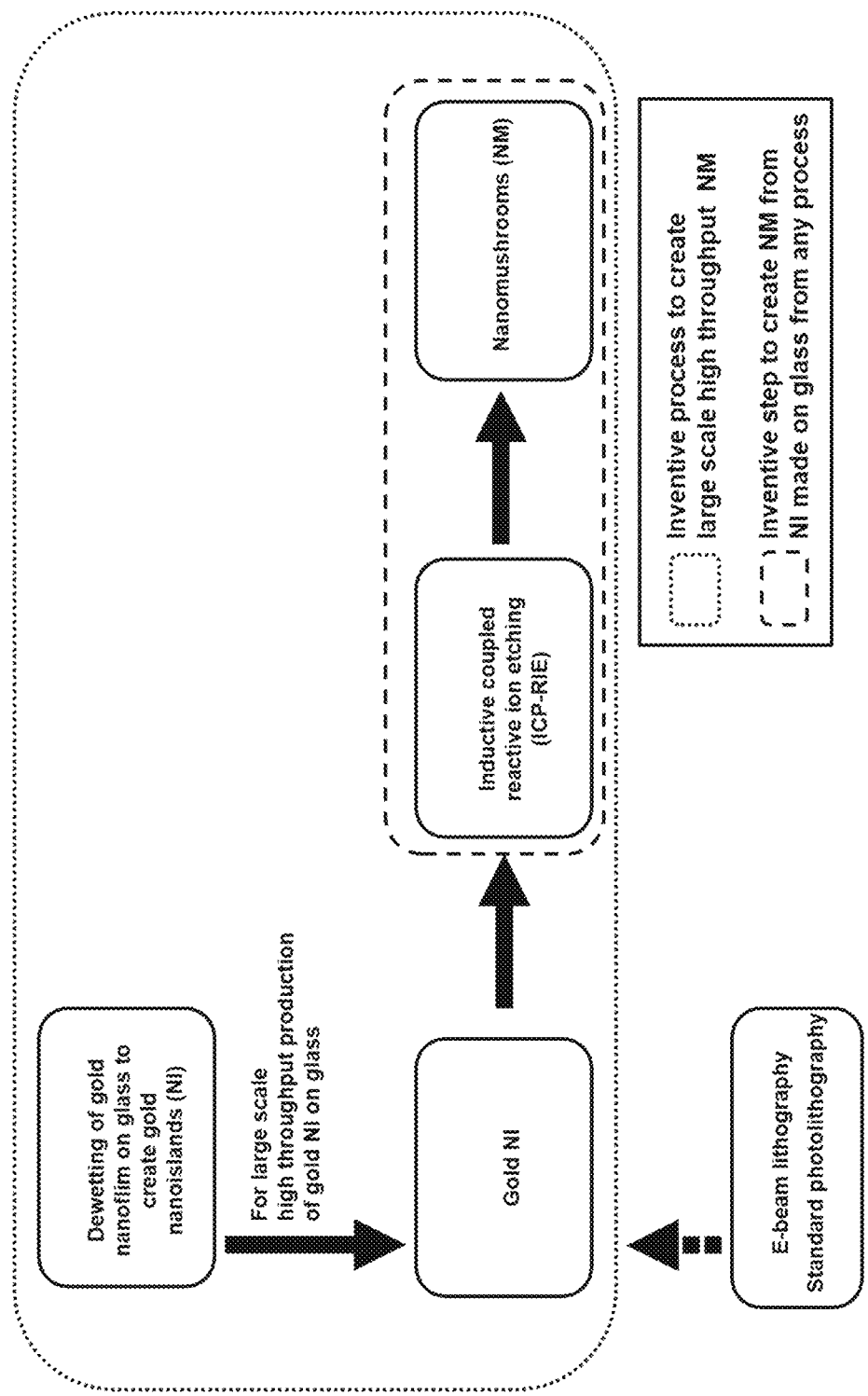

[FIG. 7]
Glass substrate
Gold deposition
annealing of gold plate
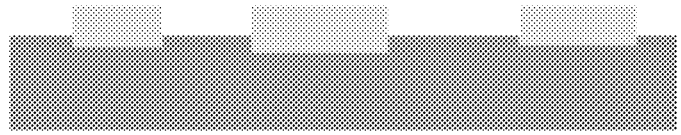
RIE of
annealed gold plate
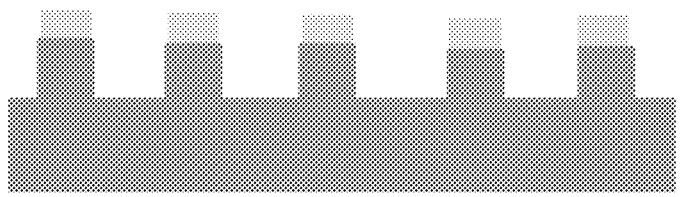

[FIG. 8]
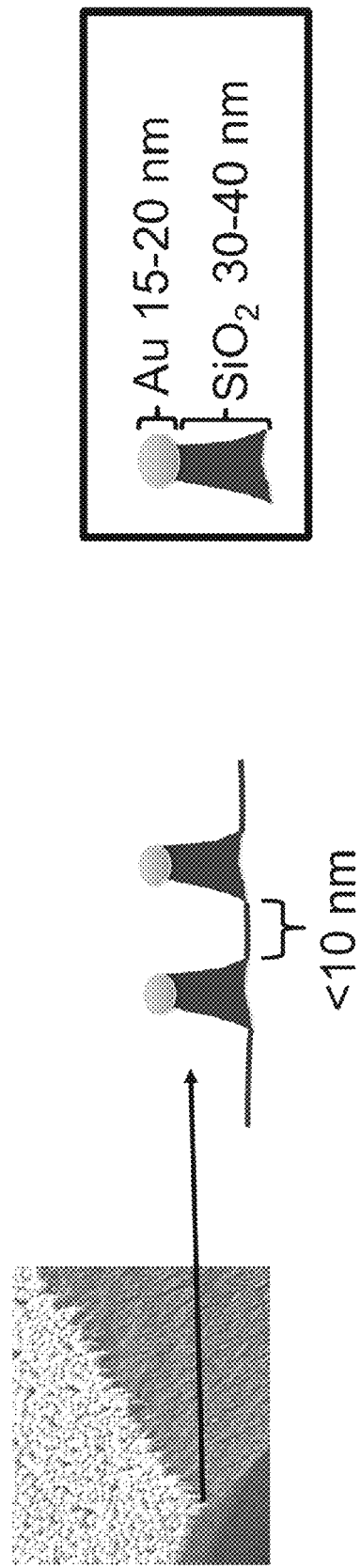

[FIG. 9(a)]
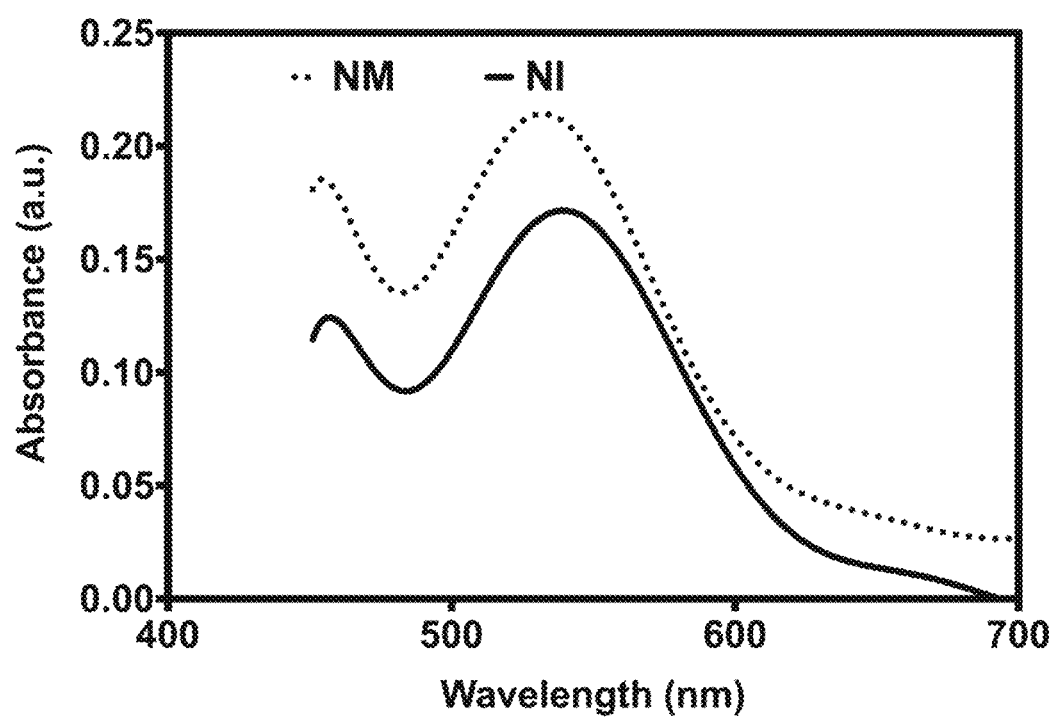

[FIG. 9(b)]
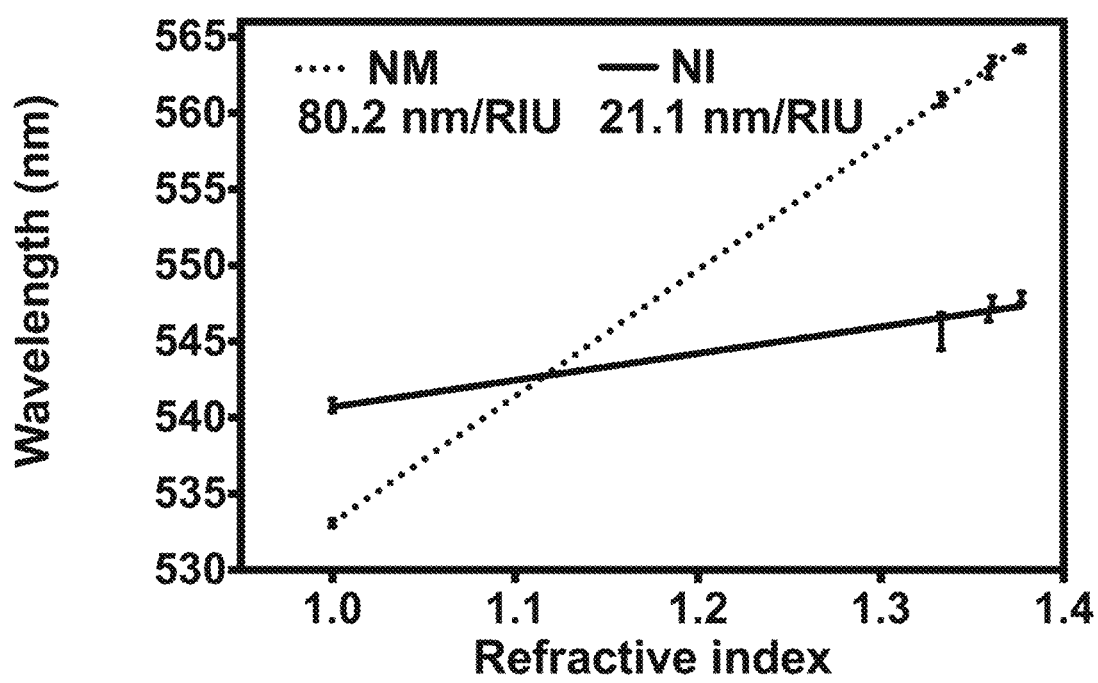

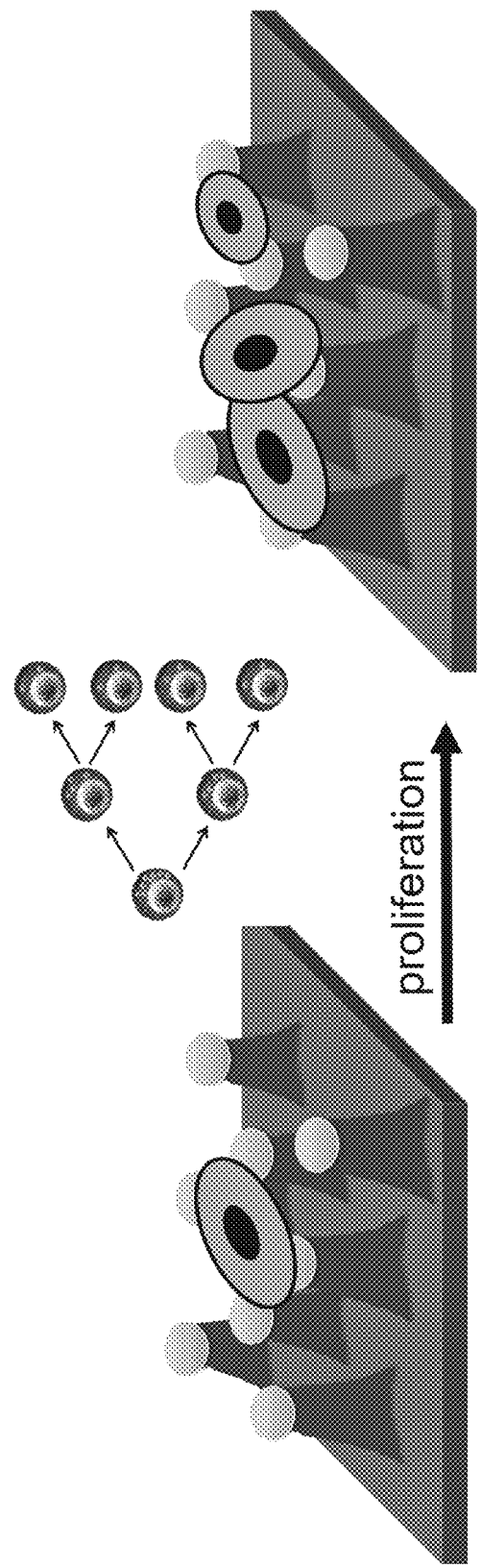
[FIG. 10]

[FIG. 11(a)]
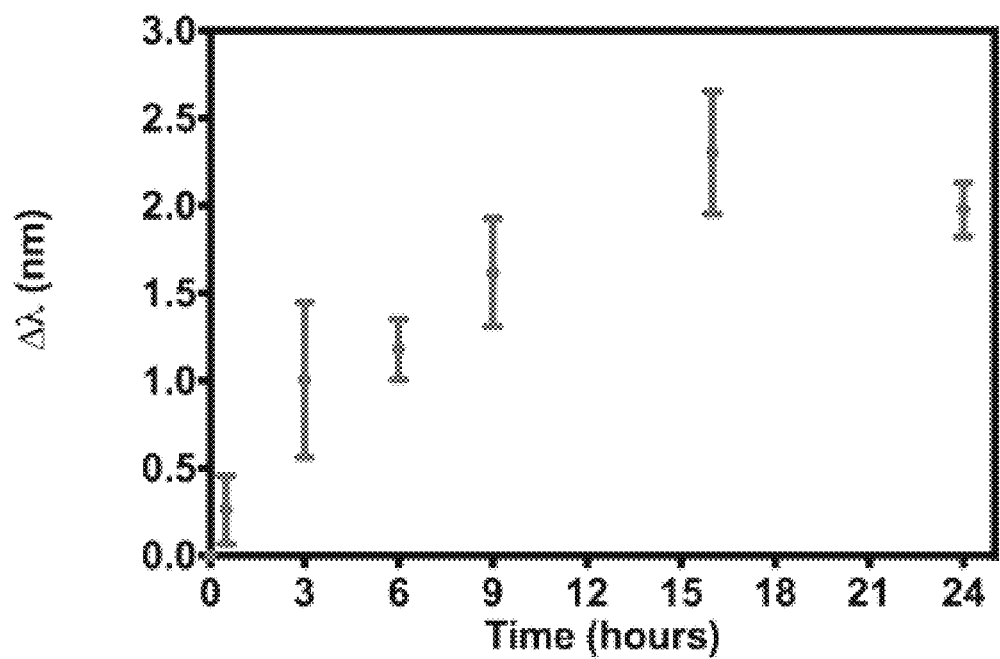

[FIG. 11(b)]
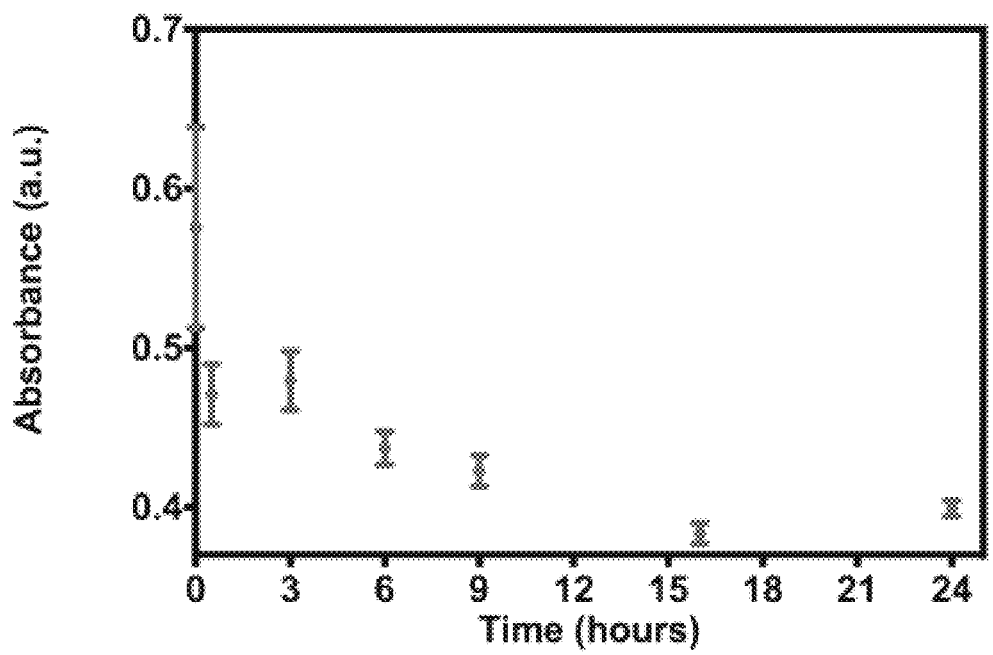

[FIG. 11(c)]
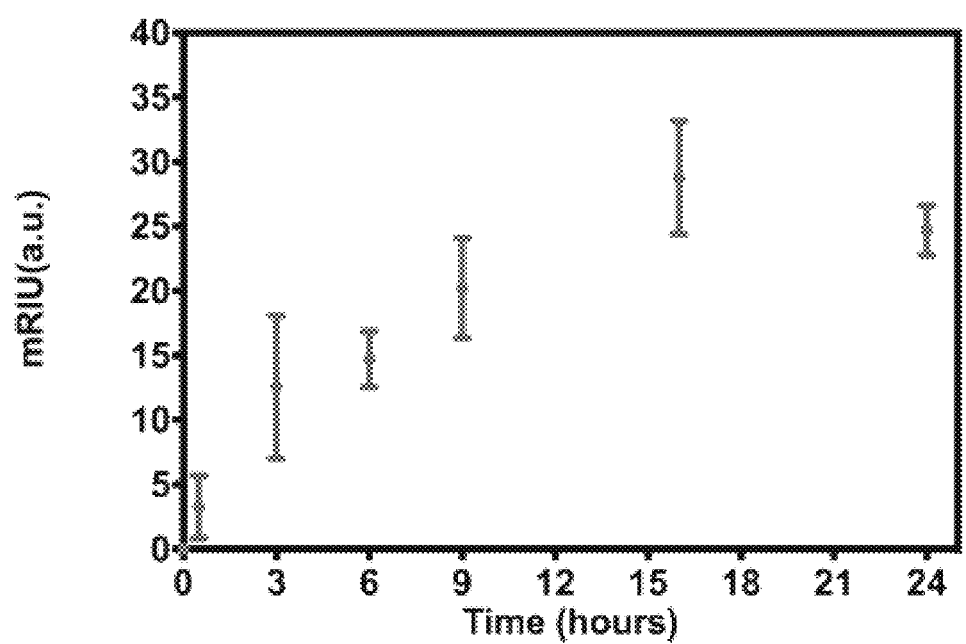

[FIG. 11(d)]
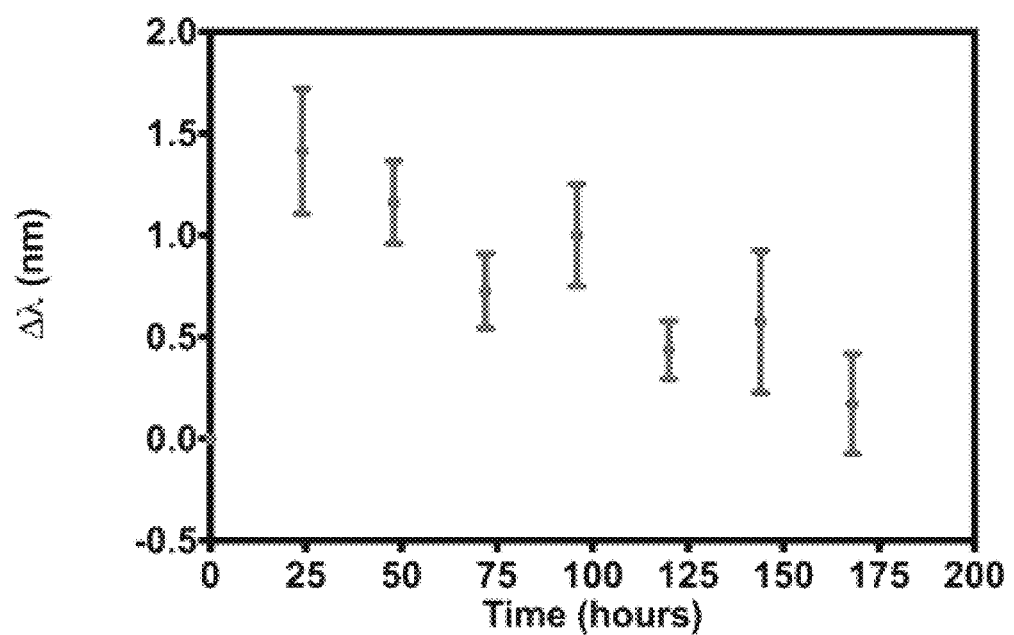

[FIG. 11(e)]
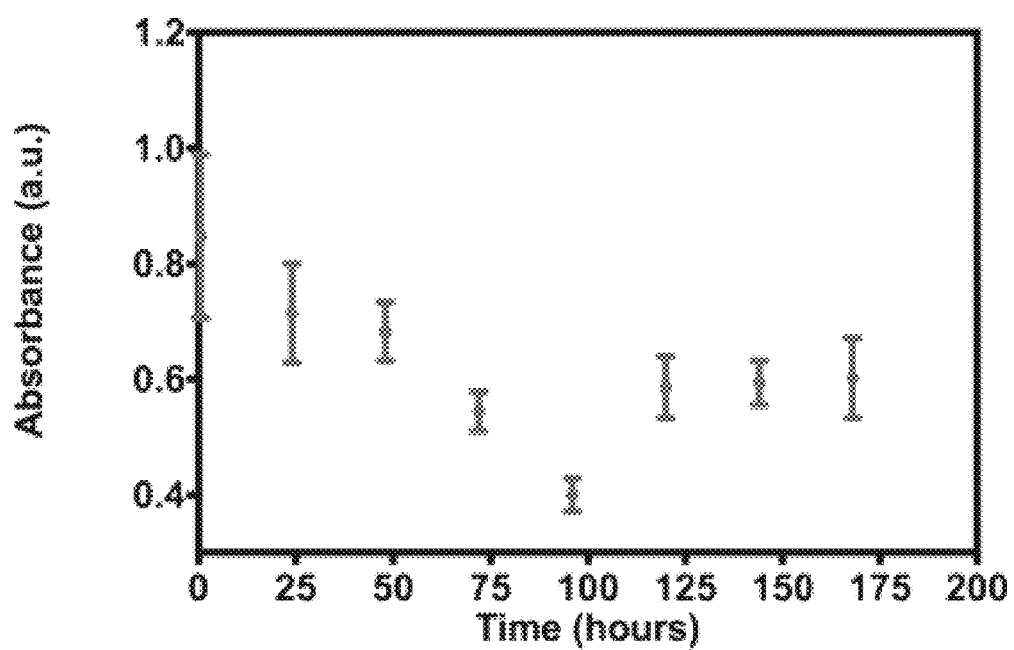

[FIG. 11(f)]
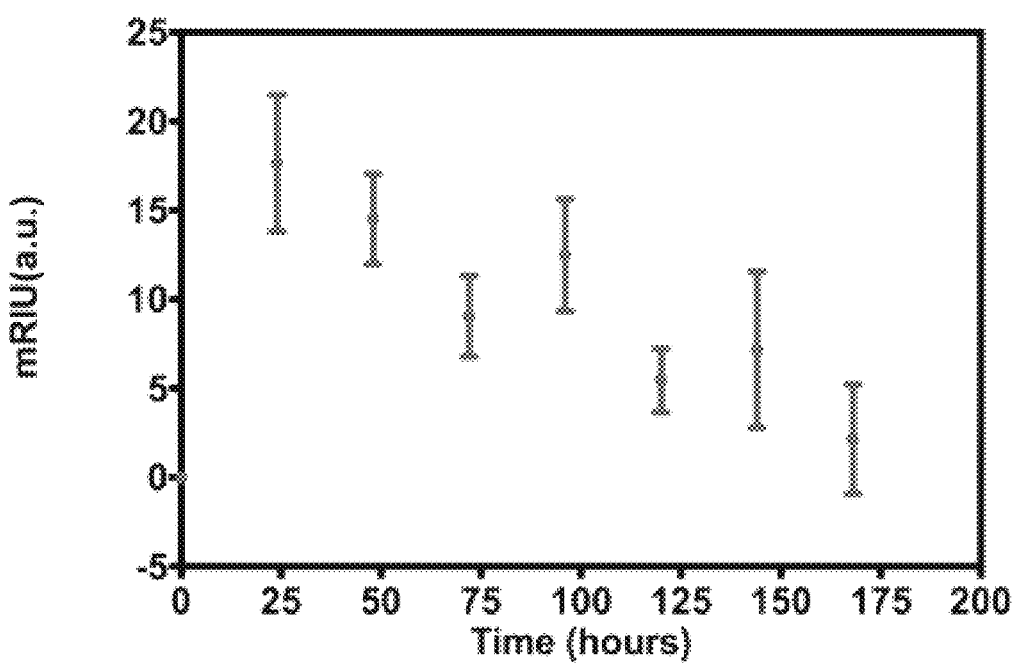

[FIG. 11(g)]
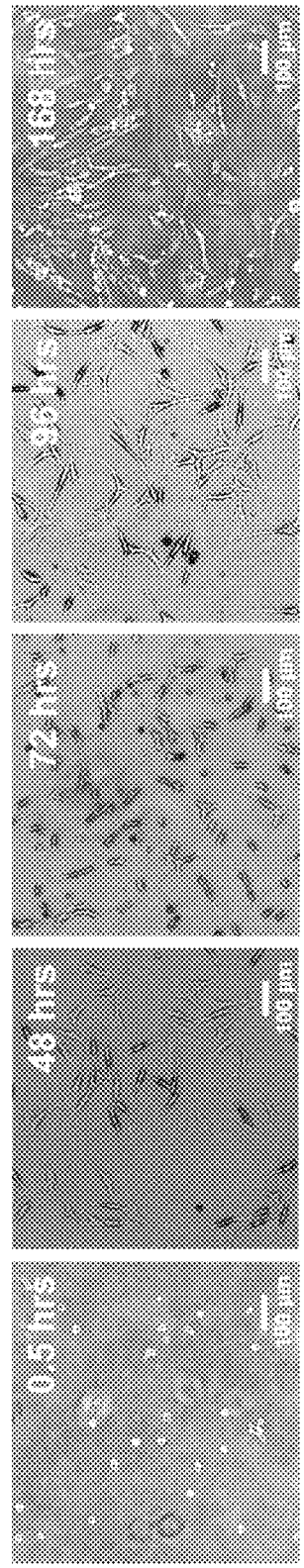

[FIG. 11(h)]
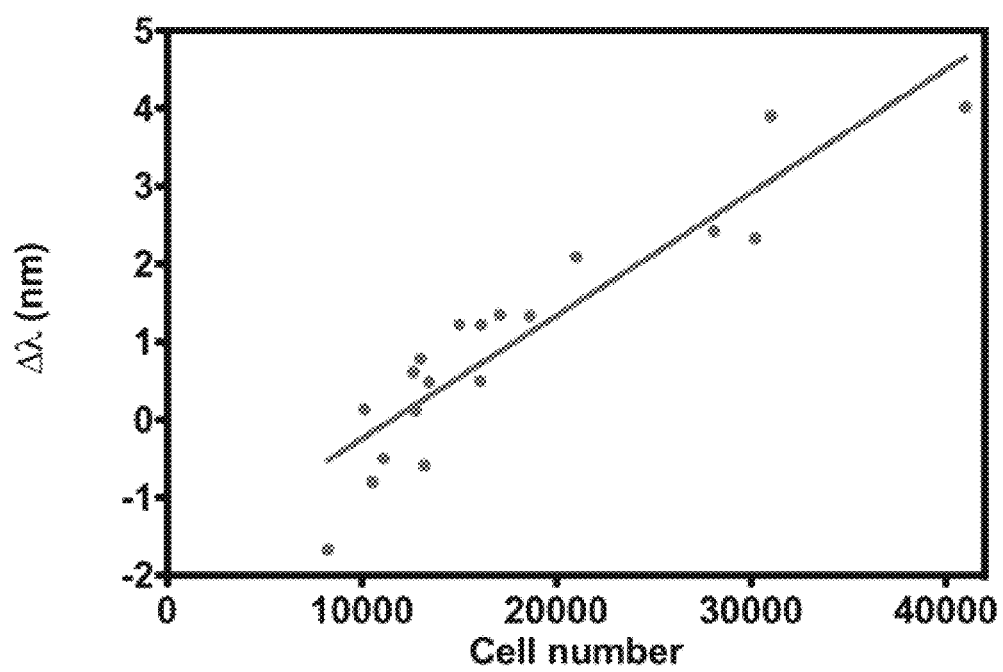

[FIG. 12]
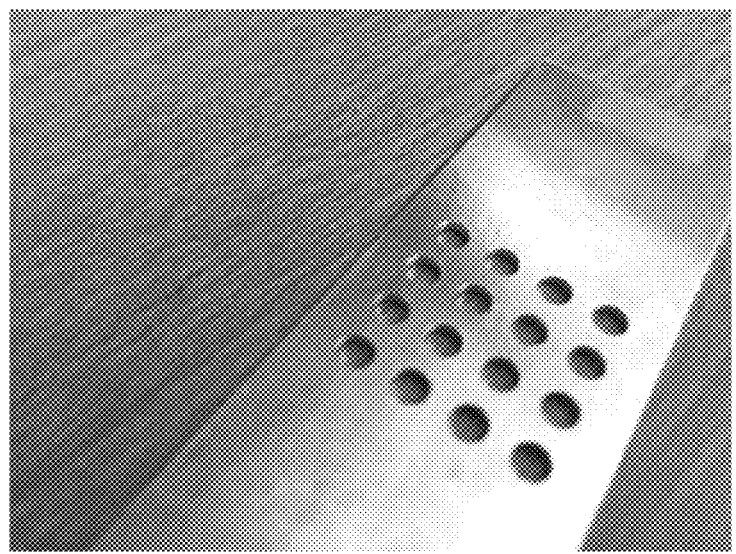

[FIG. 13]
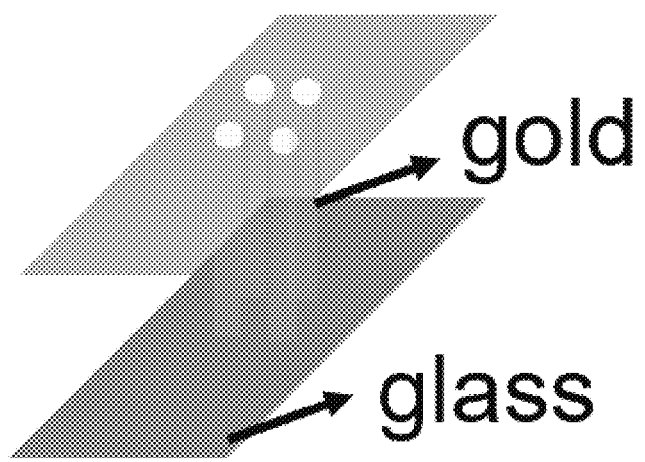

[FIG. 14]
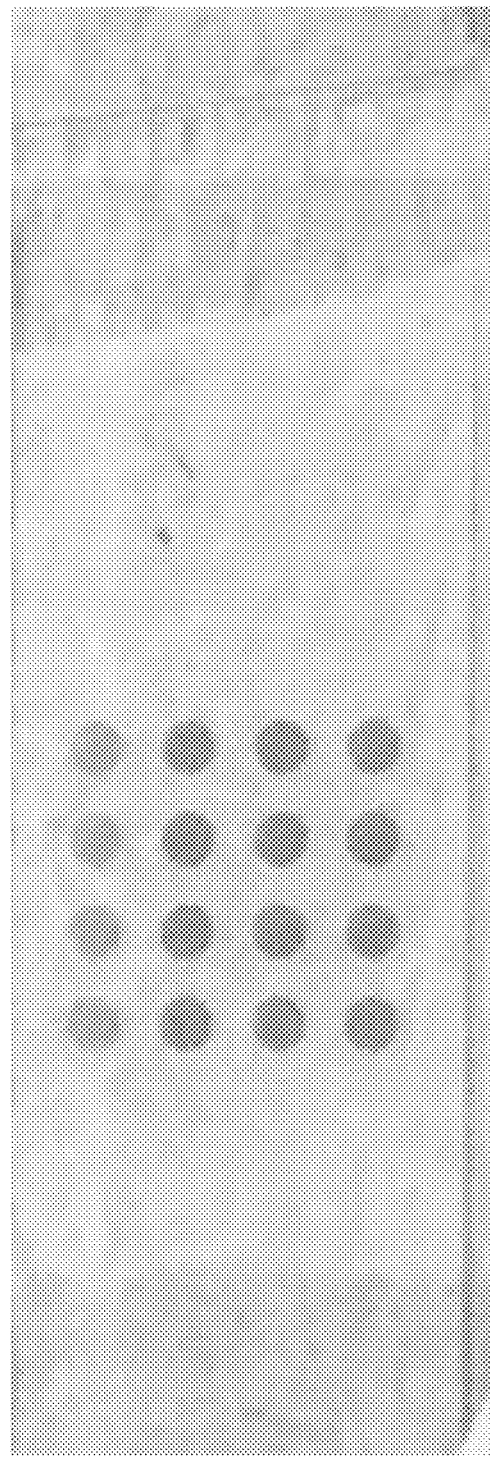

[FIG. 15]
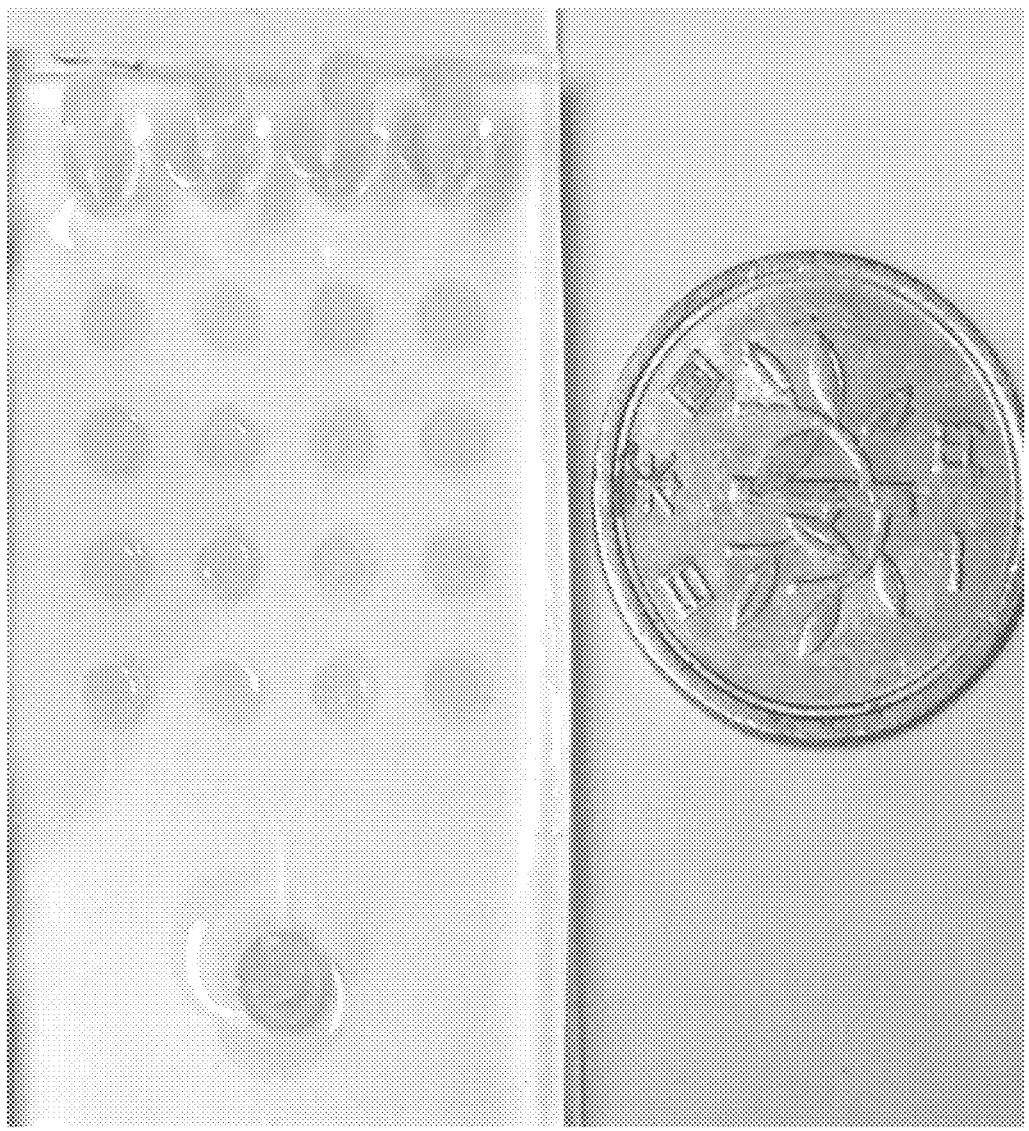

[FIG. 16]
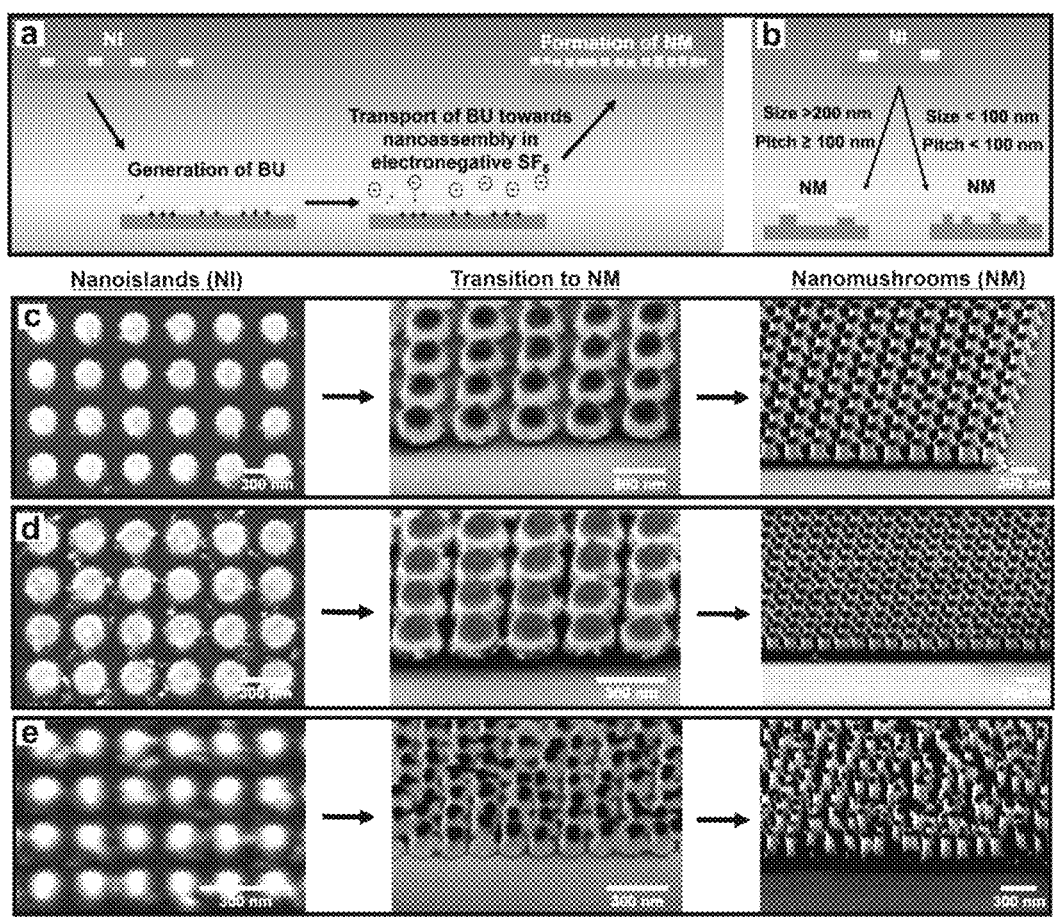

[FIG. 17(a)]
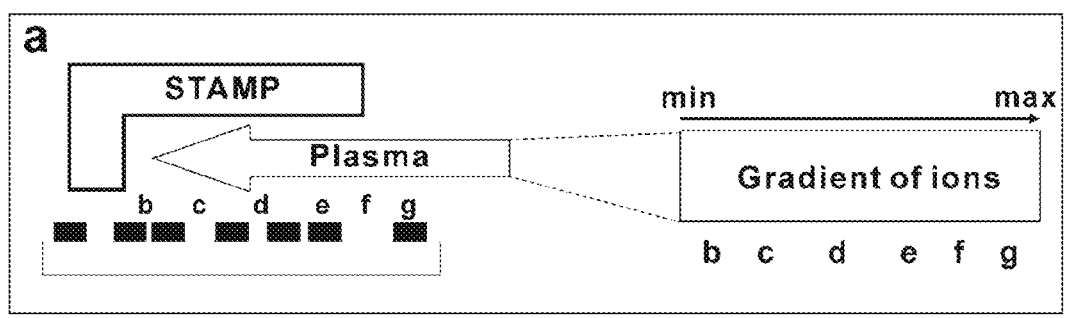

[FIG. 17(b)]
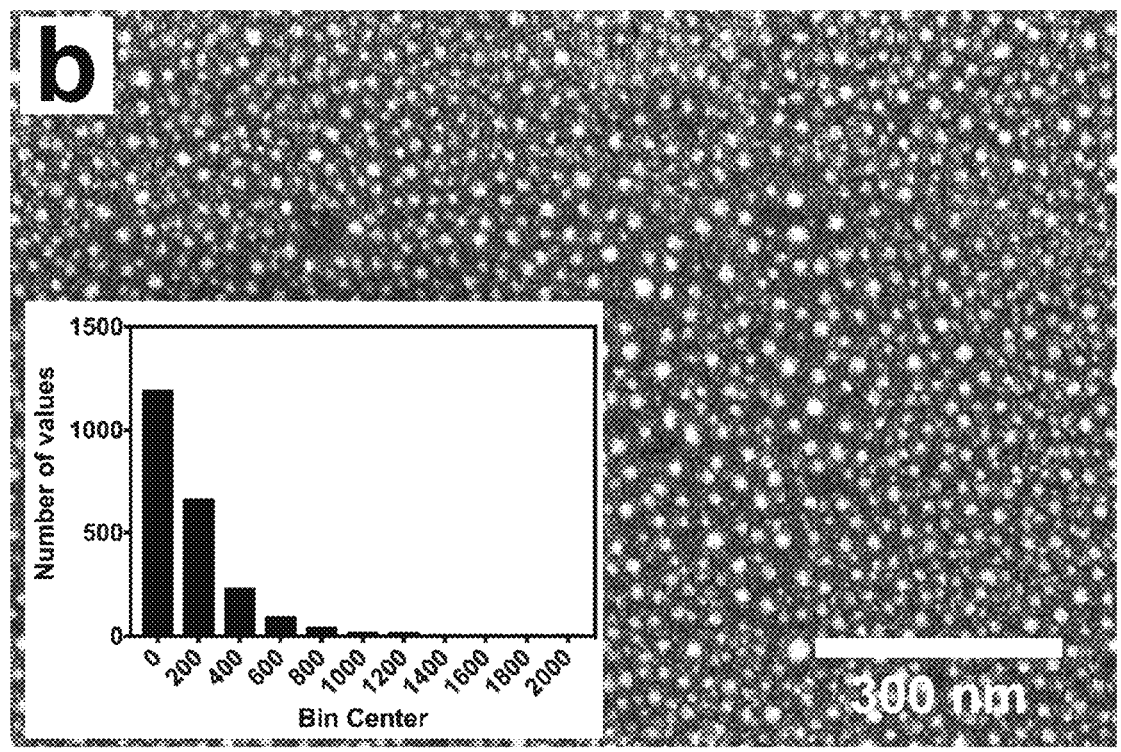

[FIG. 17(c)]
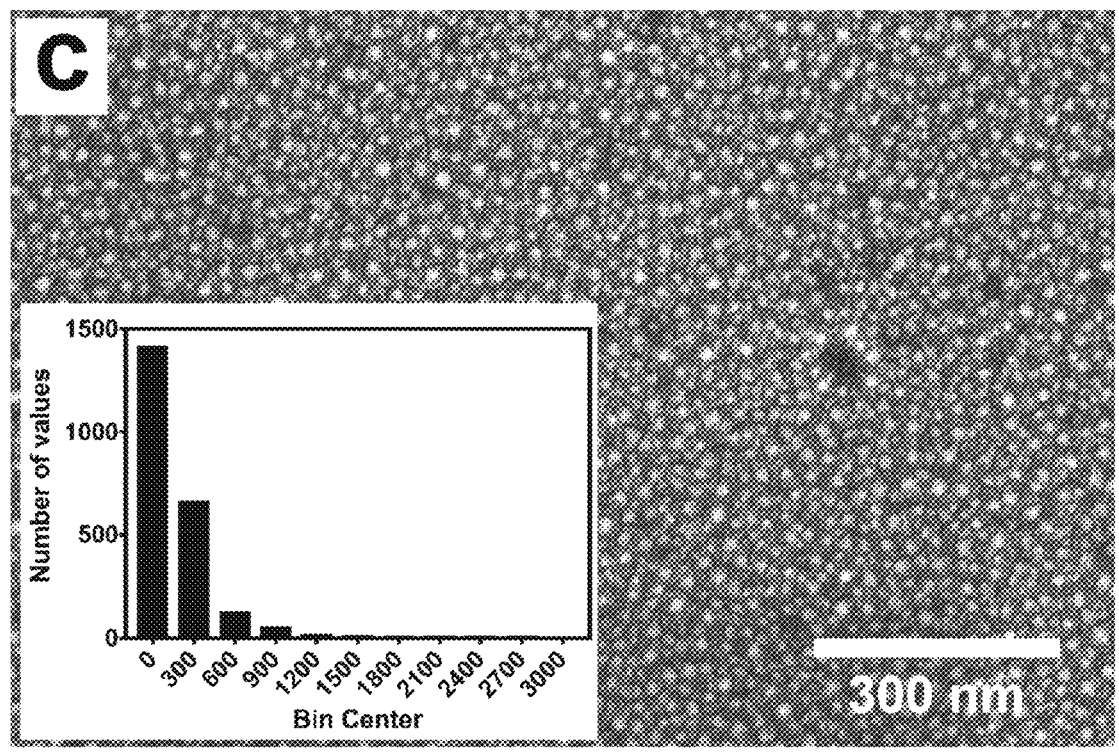

[FIG. 17(d)]
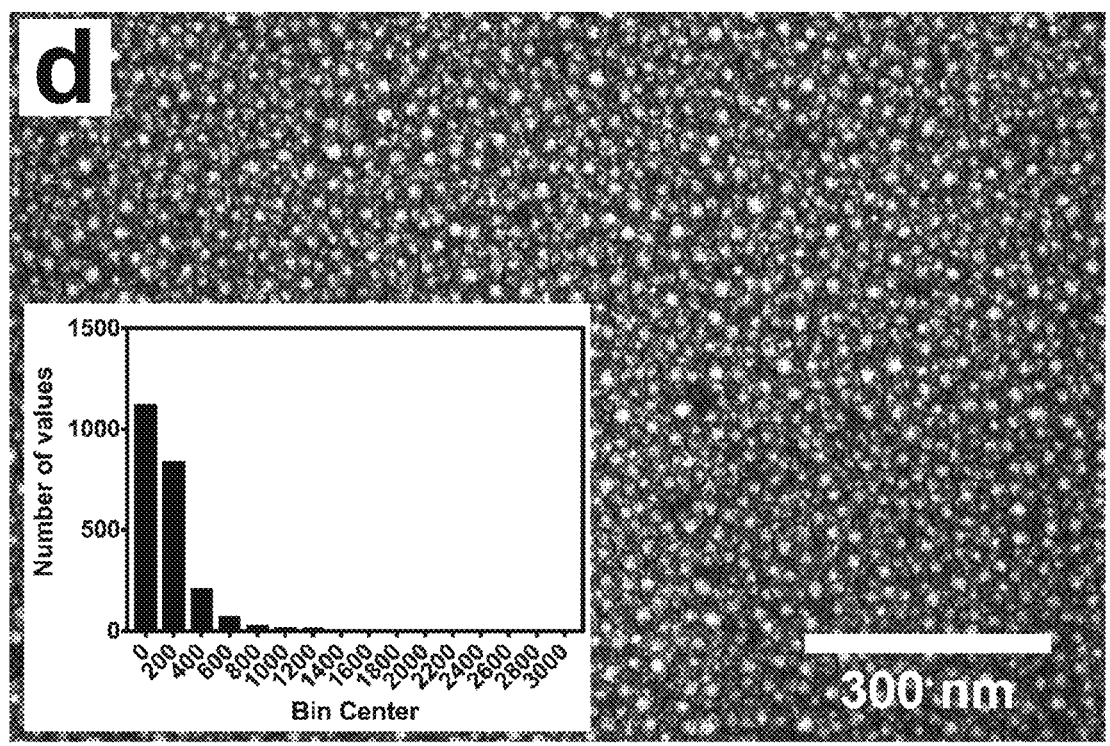

[FIG. 17(e)]
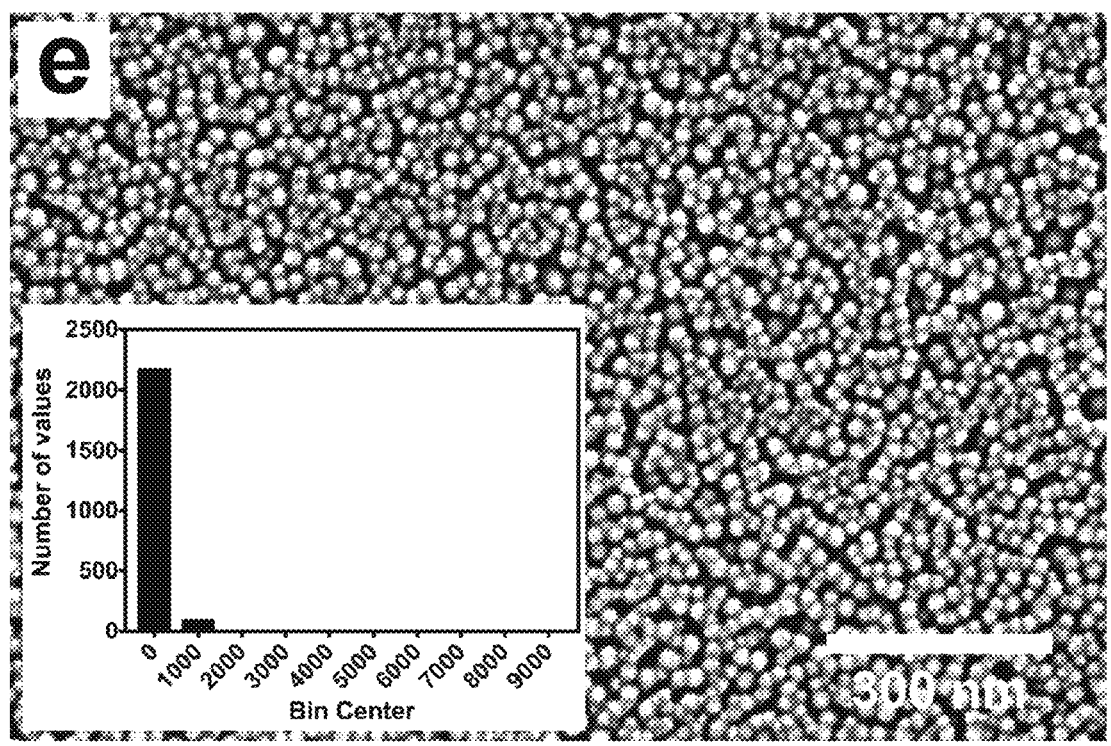

[FIG. 17(f)]
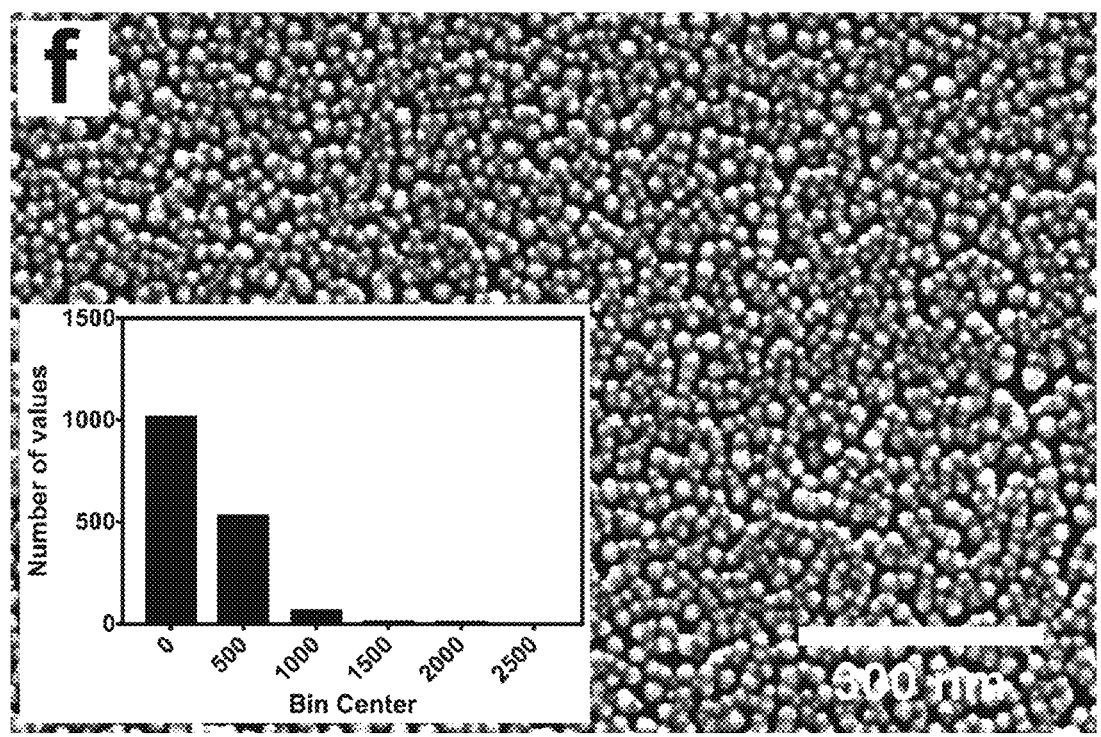

[FIG. 17(g)]
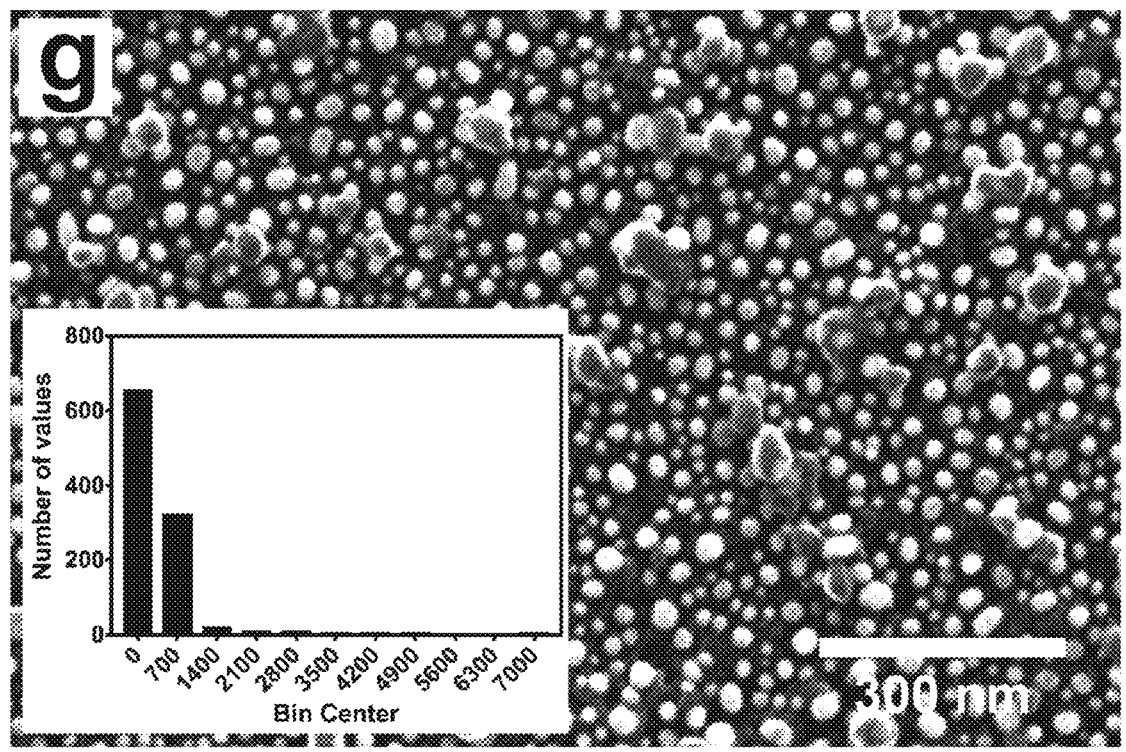

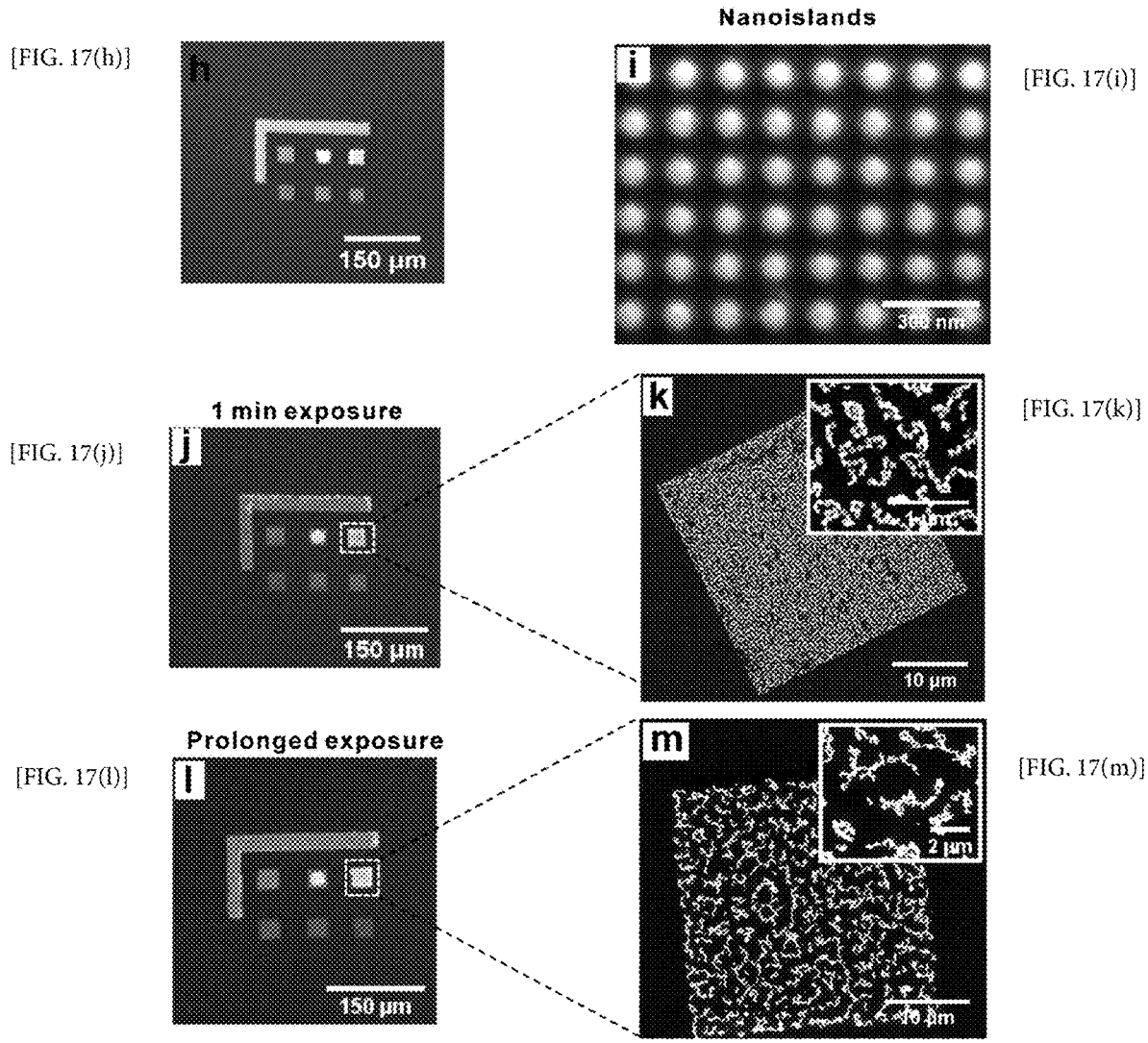

[FIG. 18(a)]
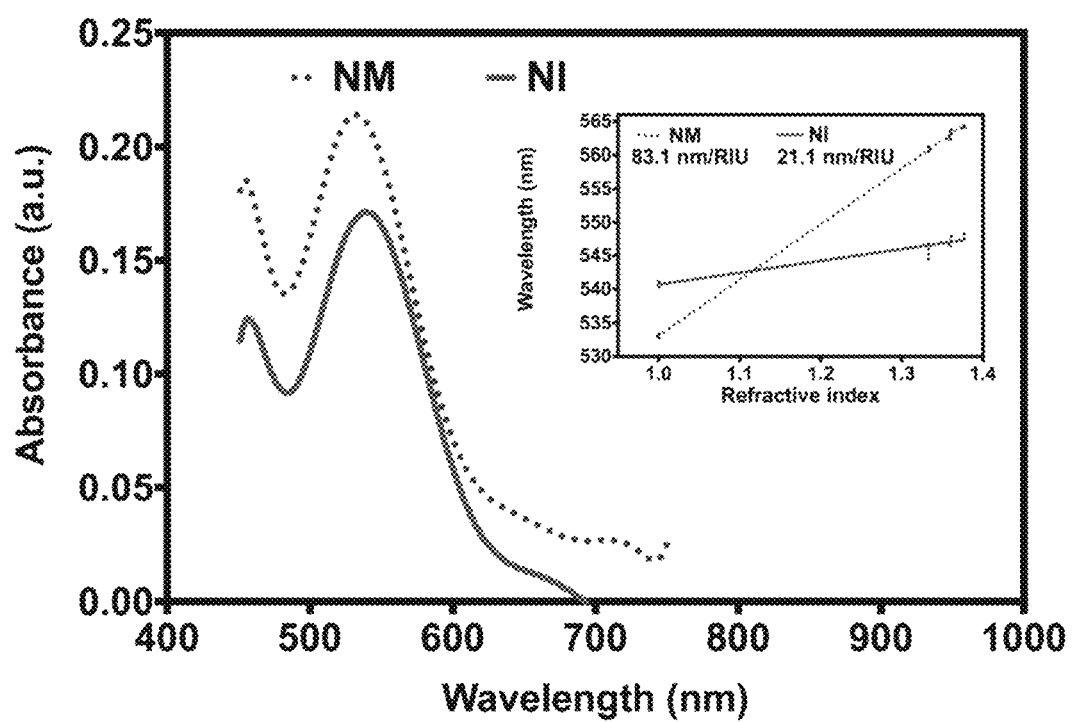

[FIG. 18(b)]
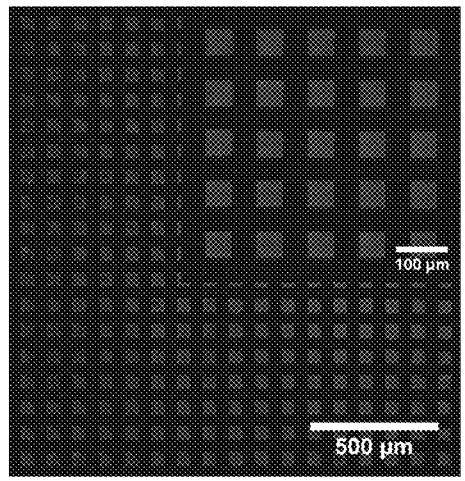
[FIG. 18(c)]
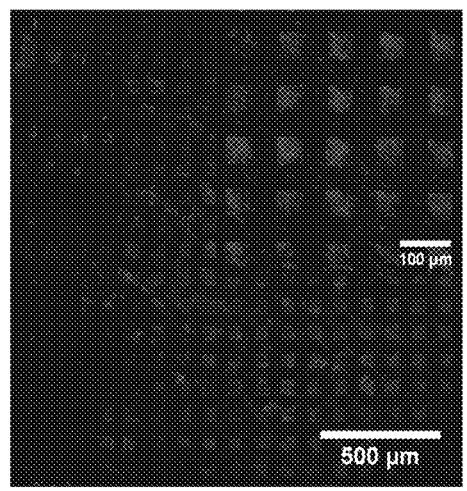
[FIG. 18(d)]
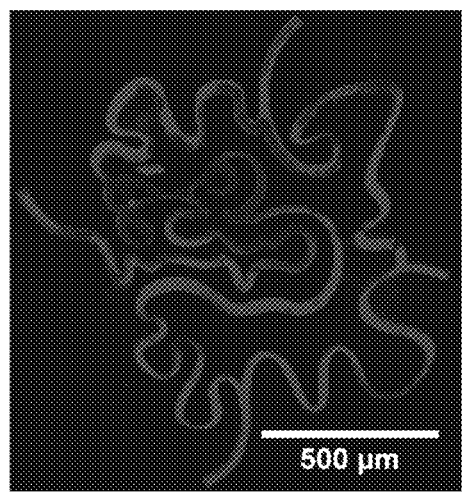
[FIG. 18(e)]
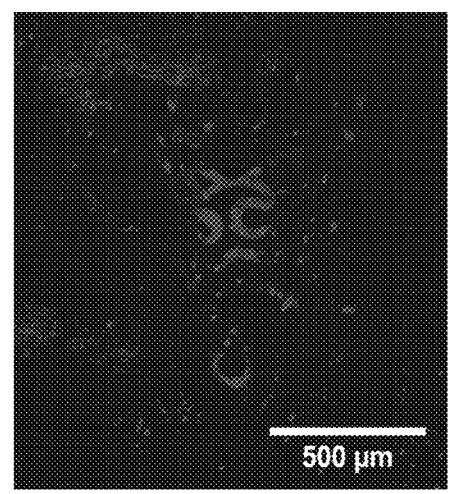

[FIG. 18(f)]
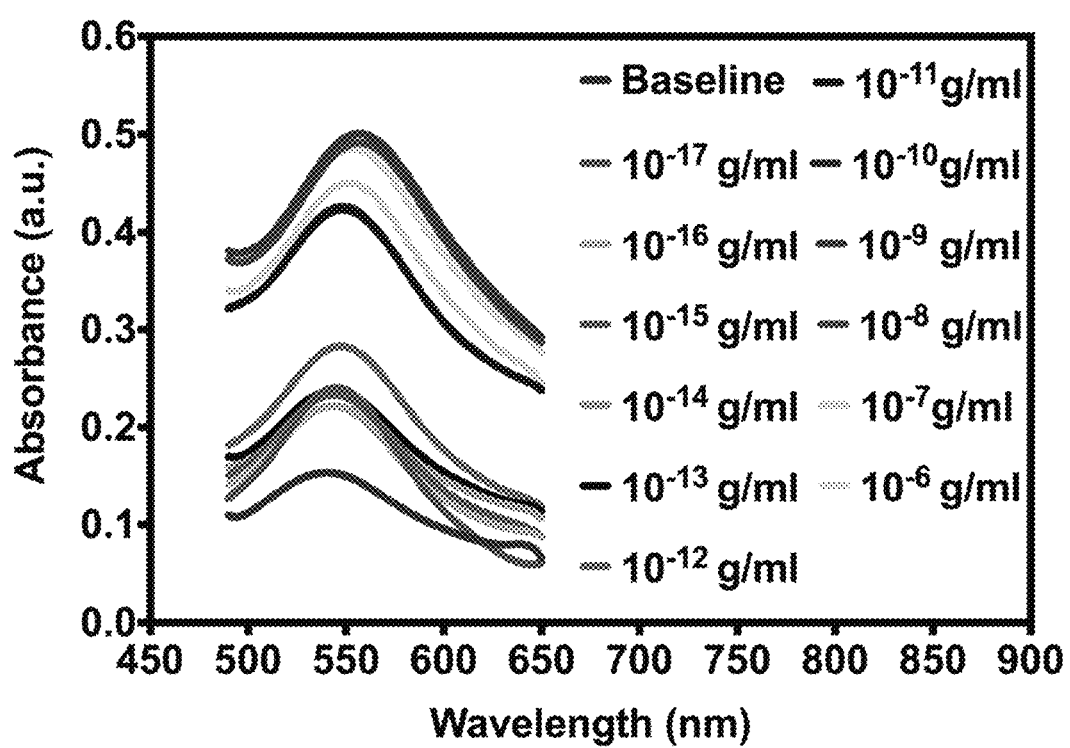

[FIG. 18(g)]
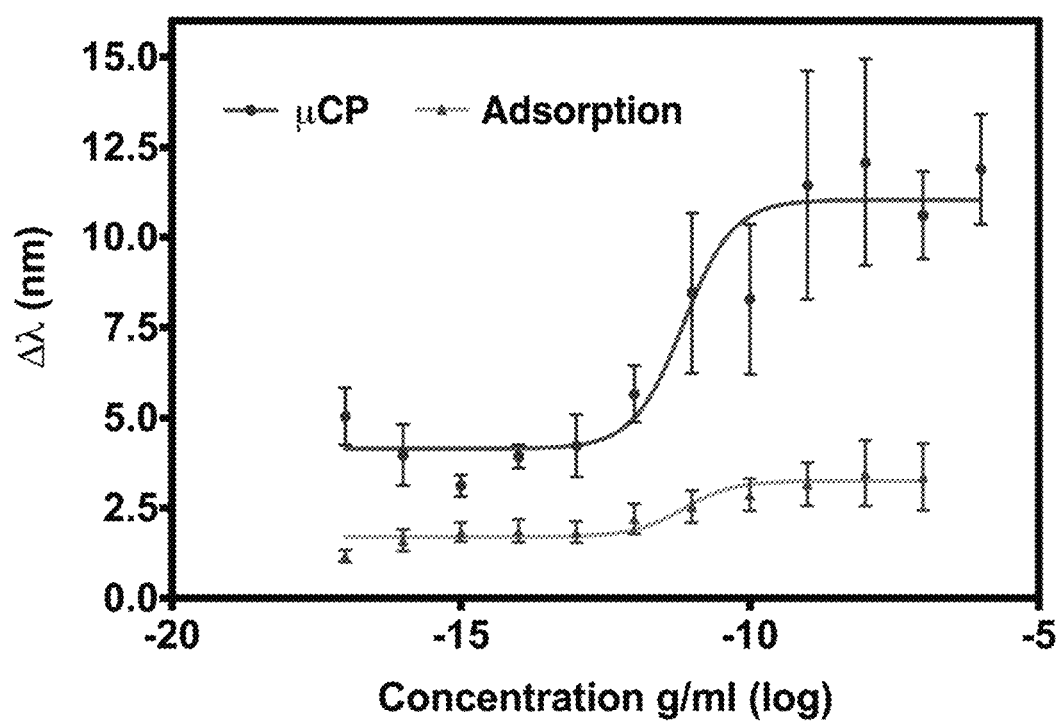

[FIG. 18(h)]
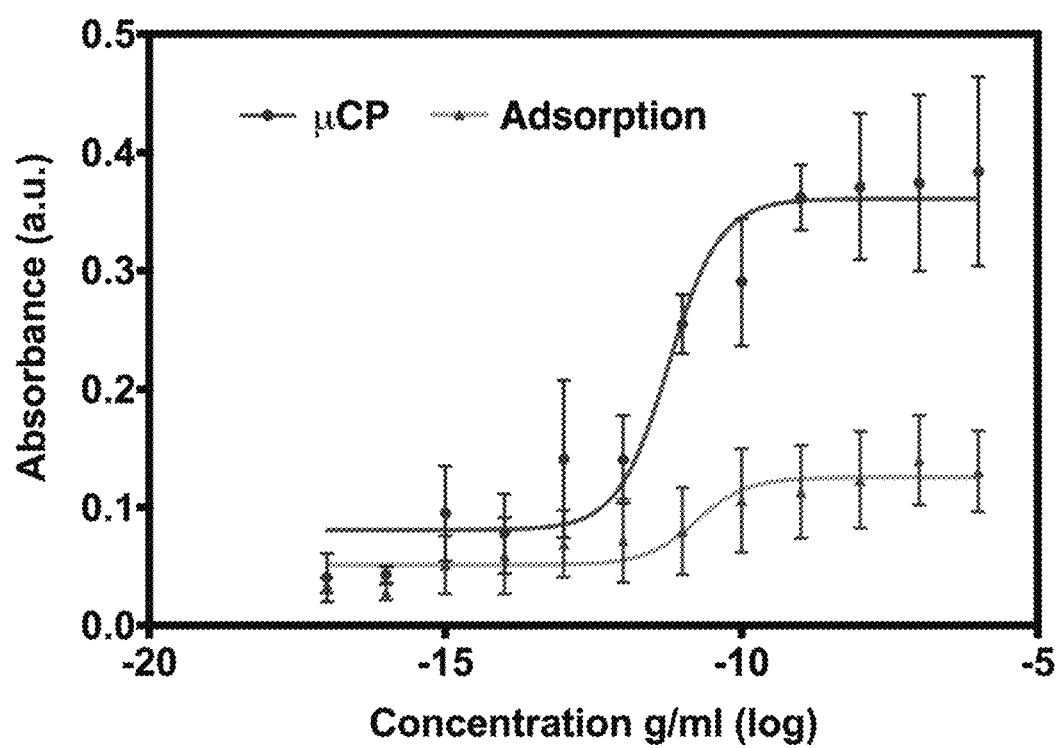

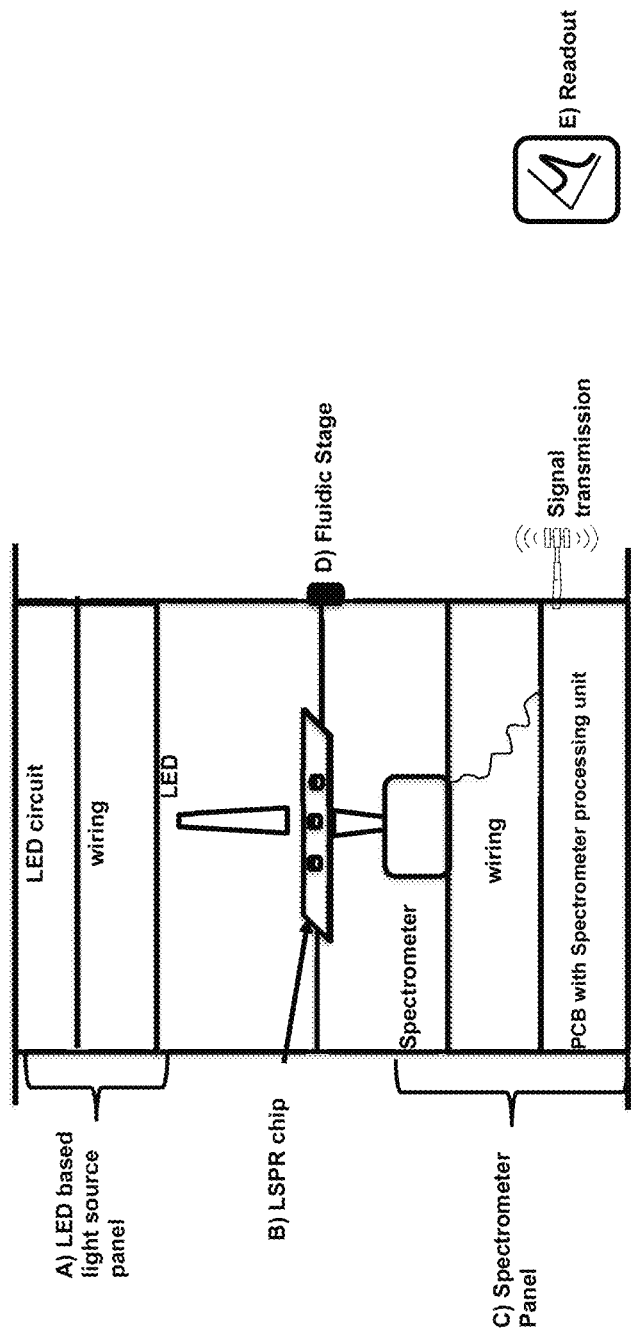
[FIG. 19]

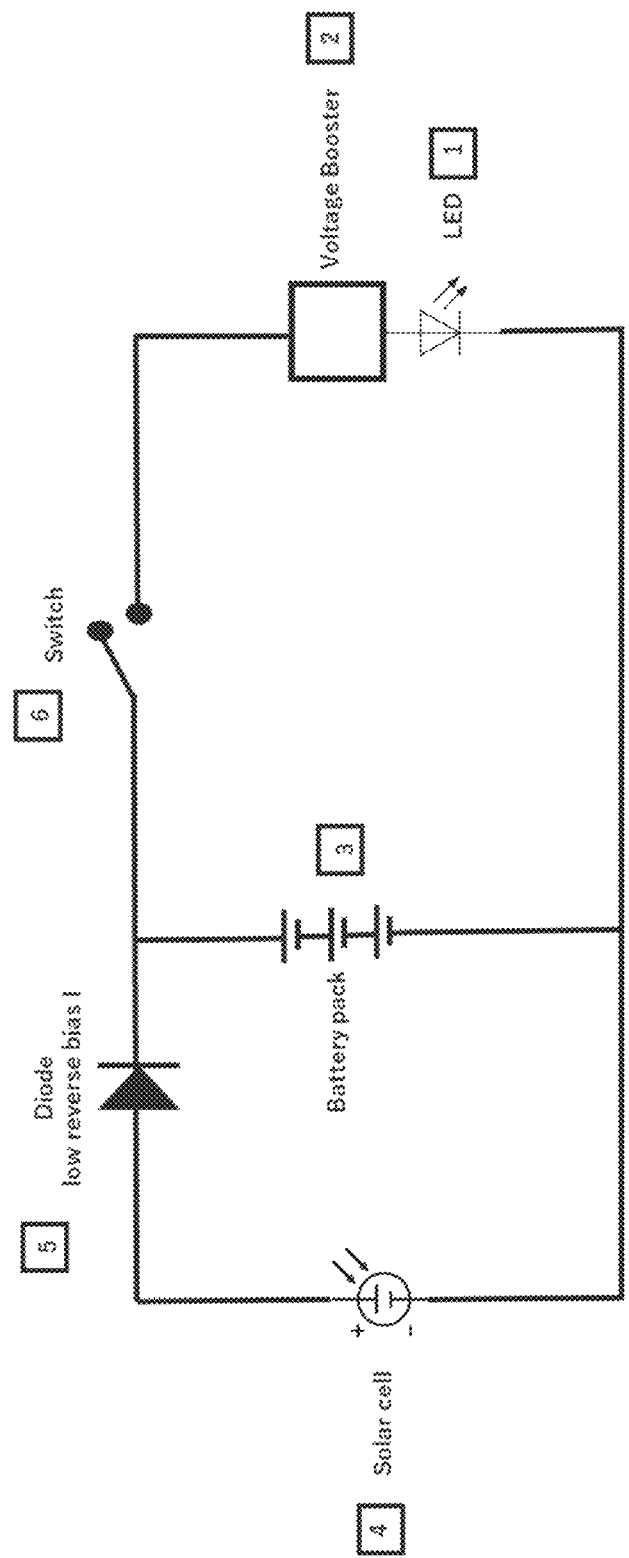
[FIG. 20]

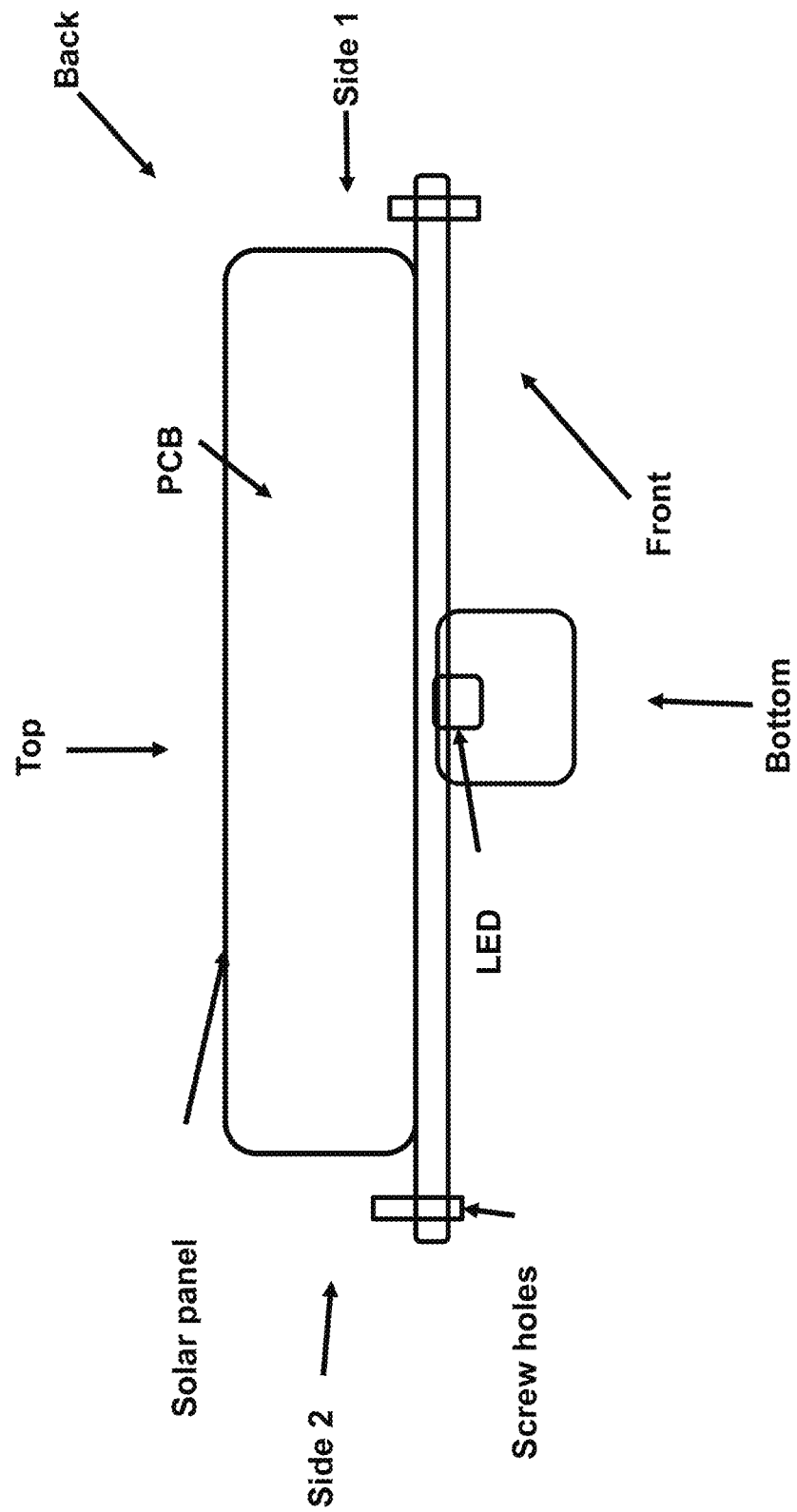
[FIG. 21]

[FIG. 22]
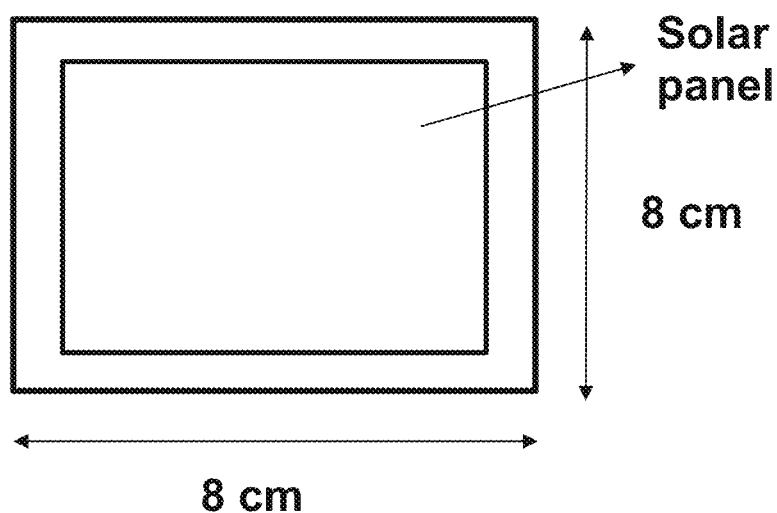
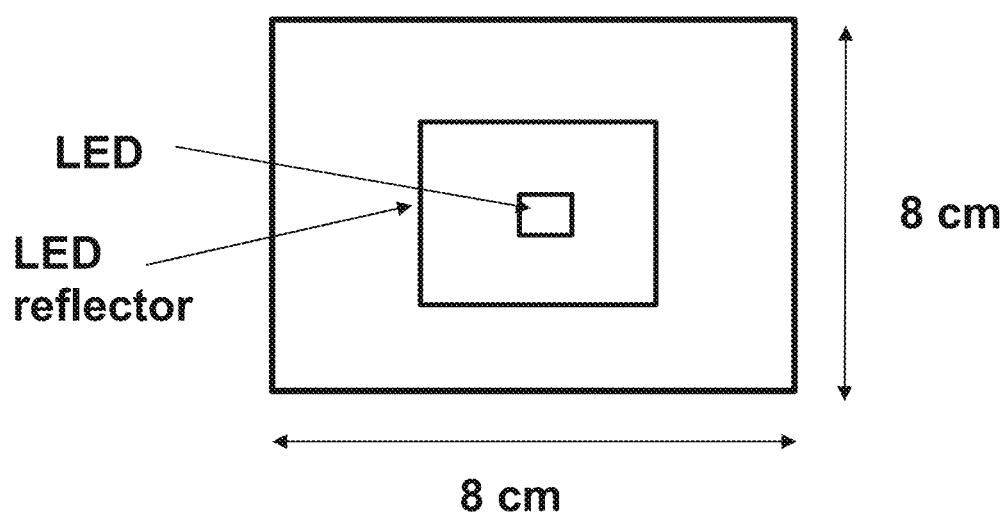

[FIG. 23]
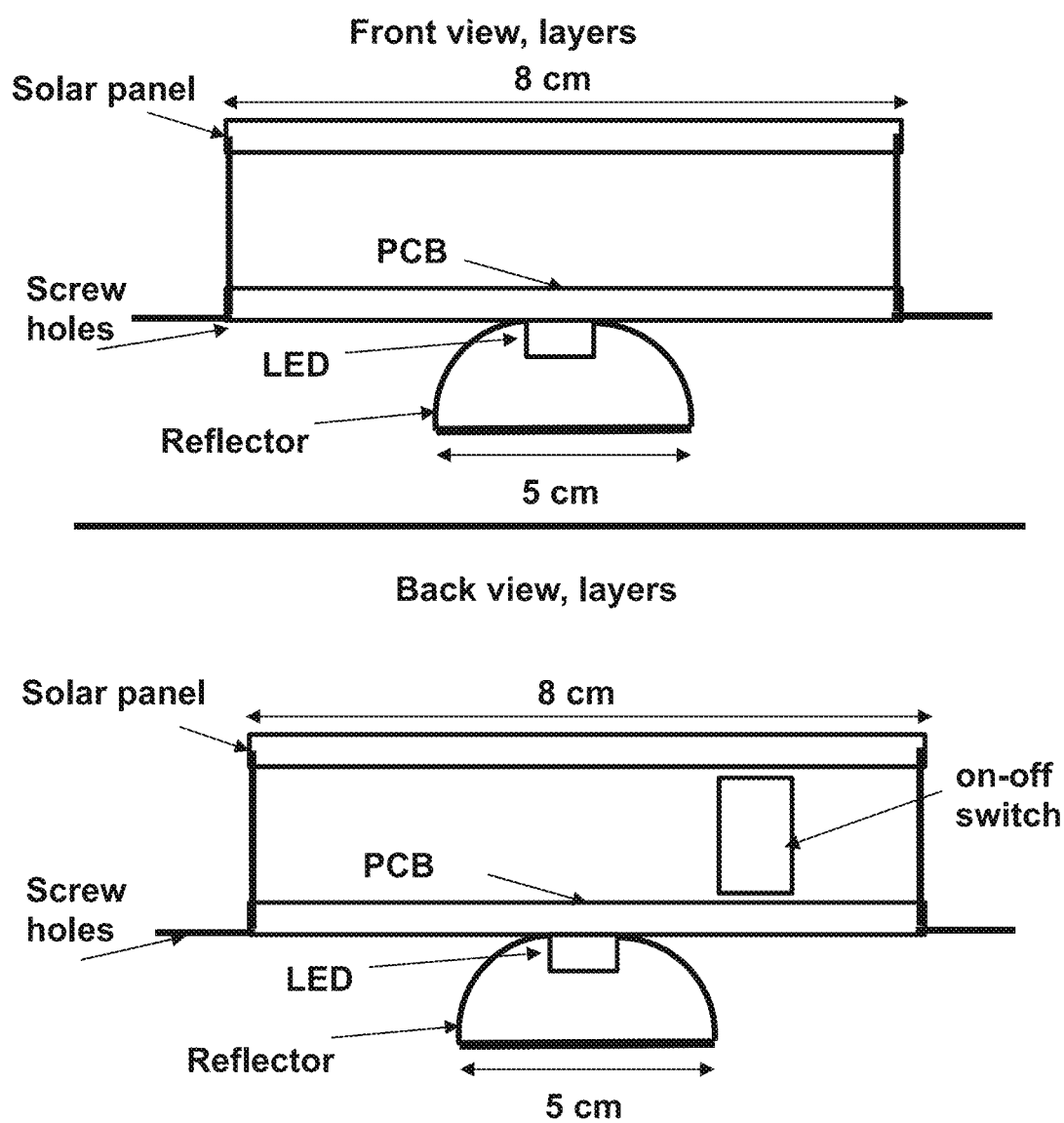

[FIG. 24]
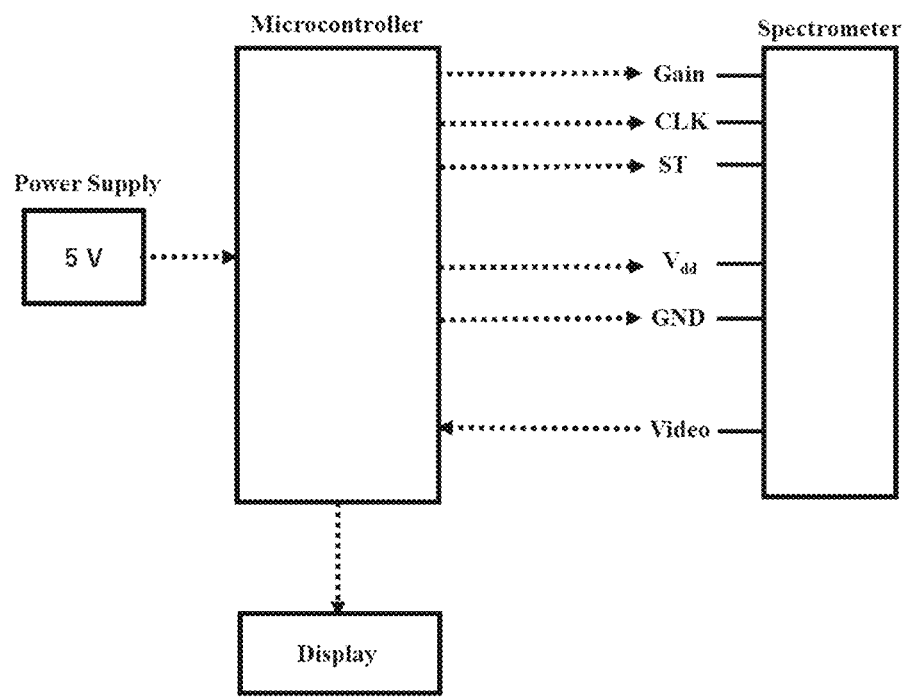

[FIG. 25(a)]
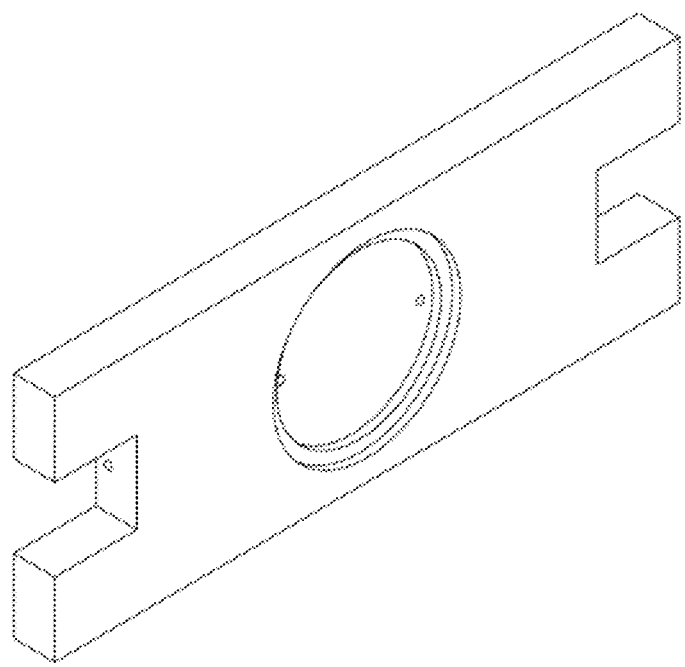

[FIG. 25(b)]
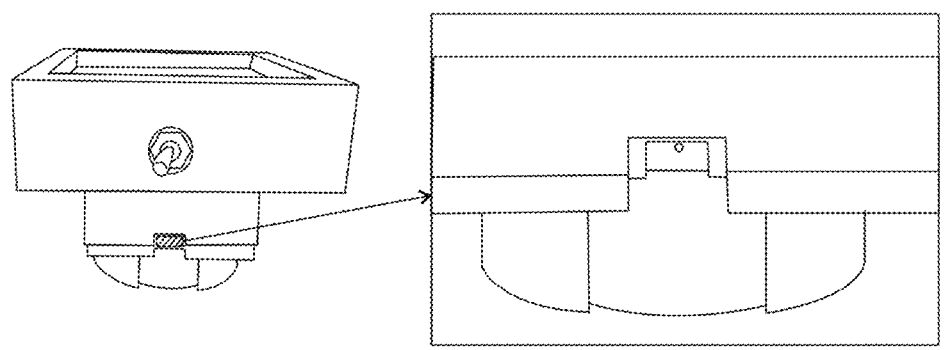

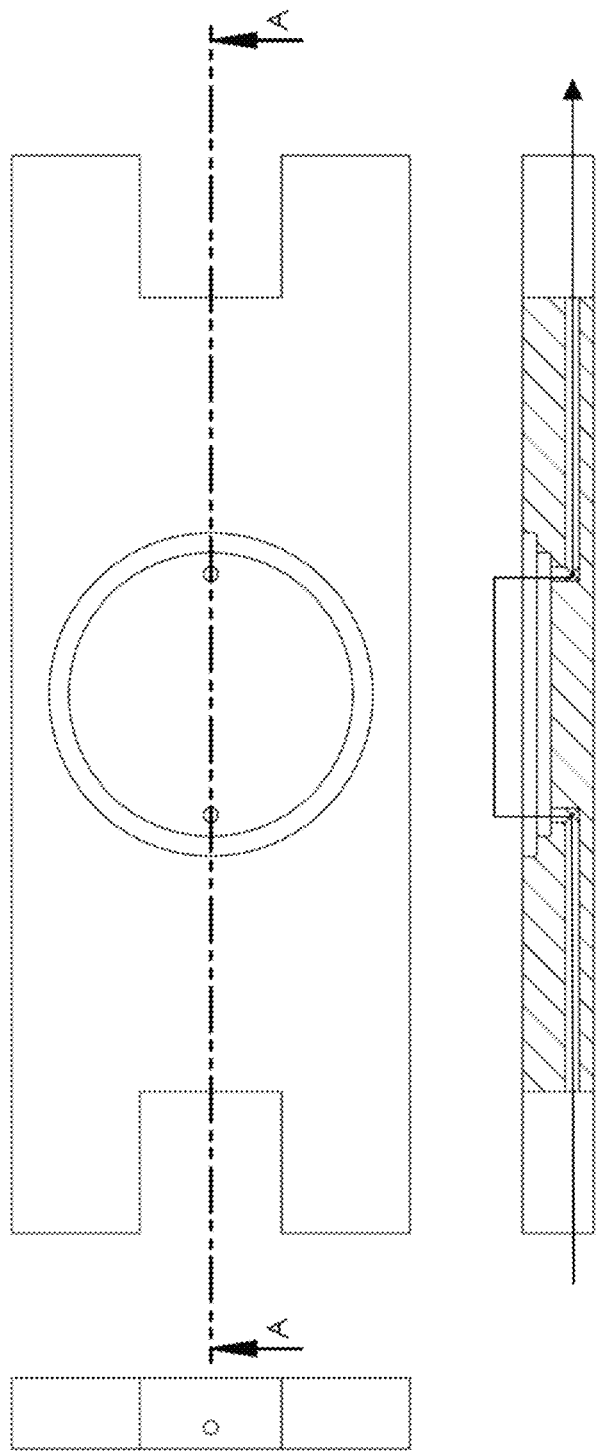
[FIG. 25(c)]

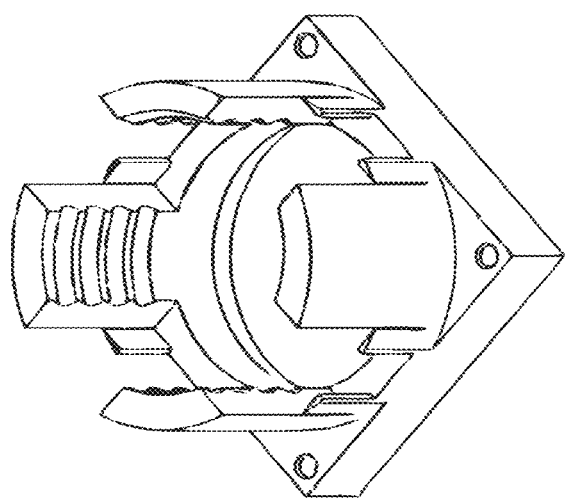
[FIG. 26(a)]
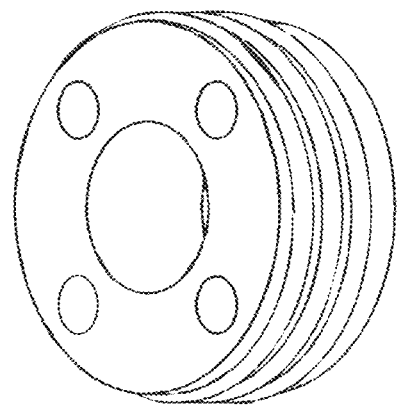
[FIG.26(b)]
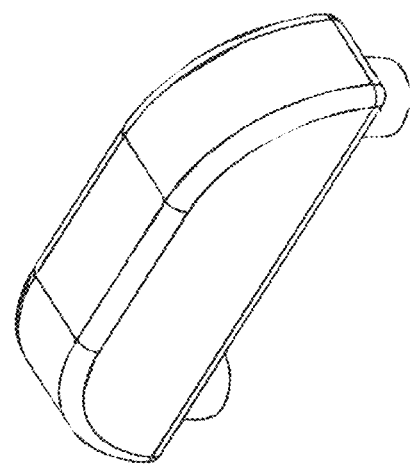
[FIG. 26(c)]

[FIG. 27]
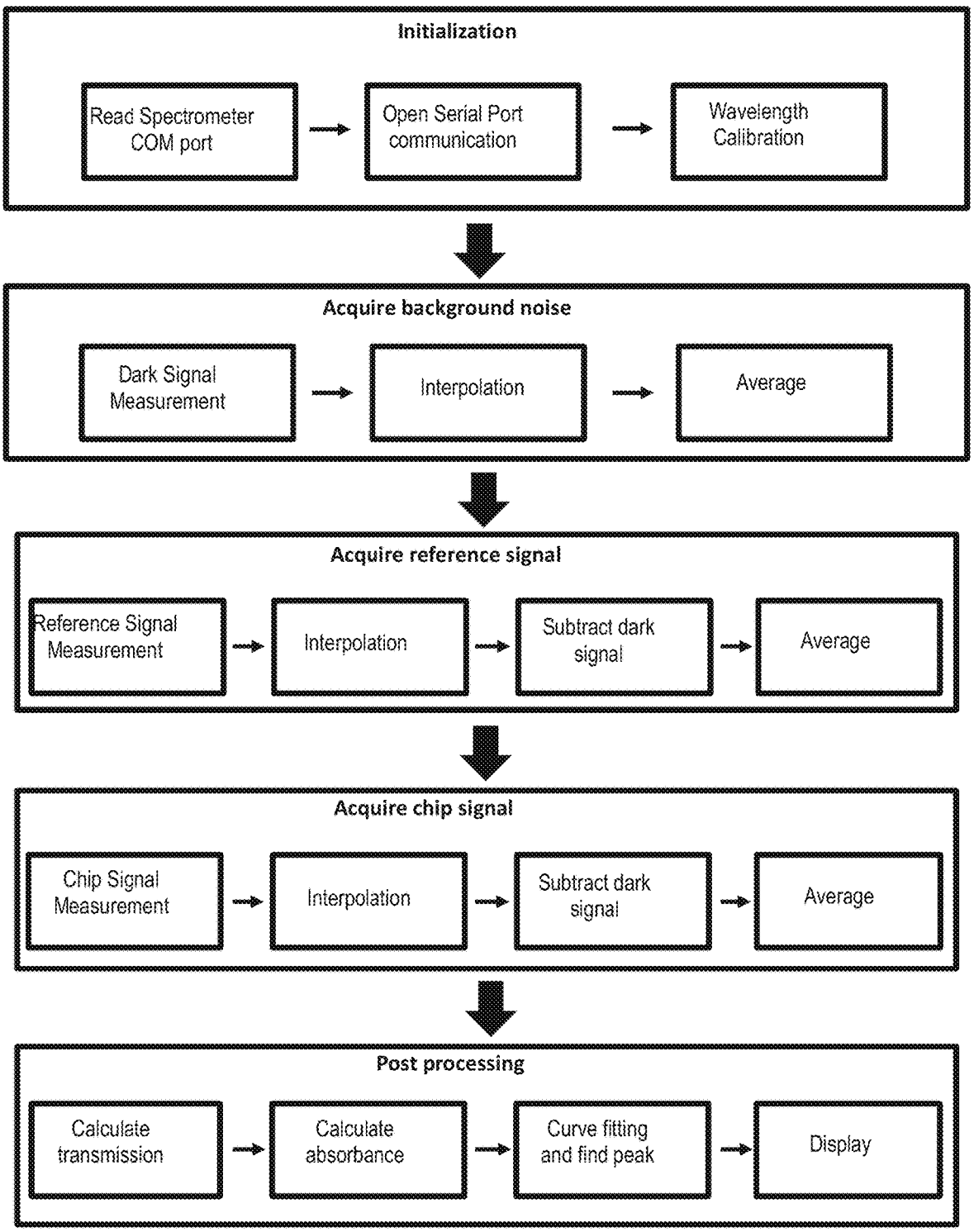

[FIG. 28]
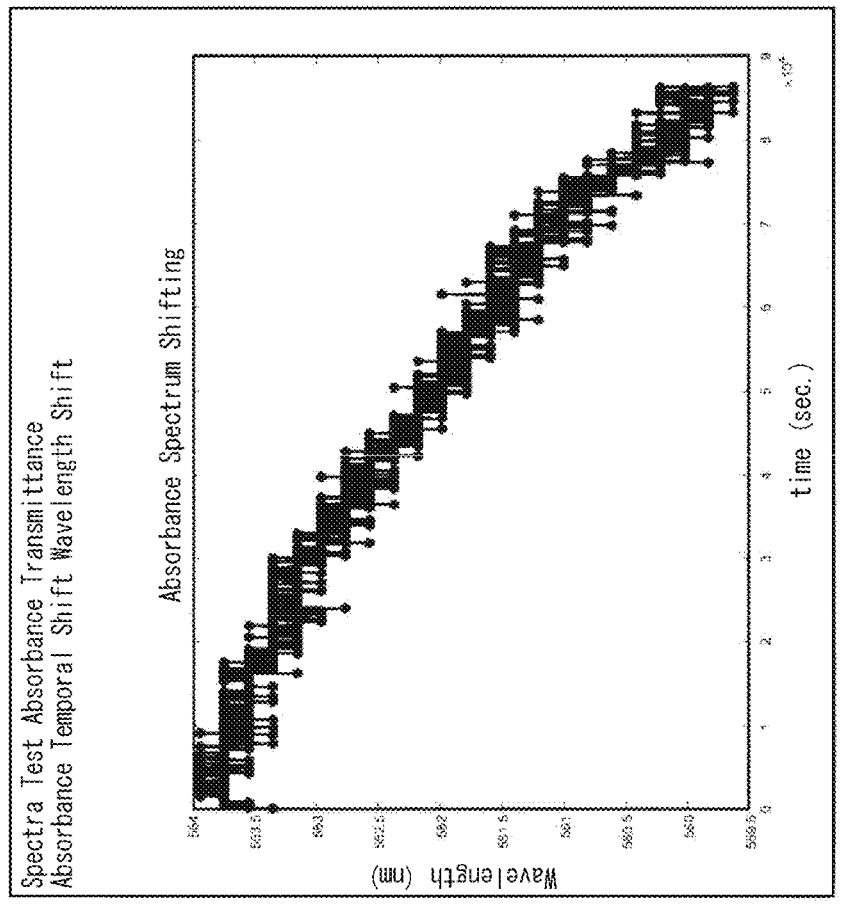
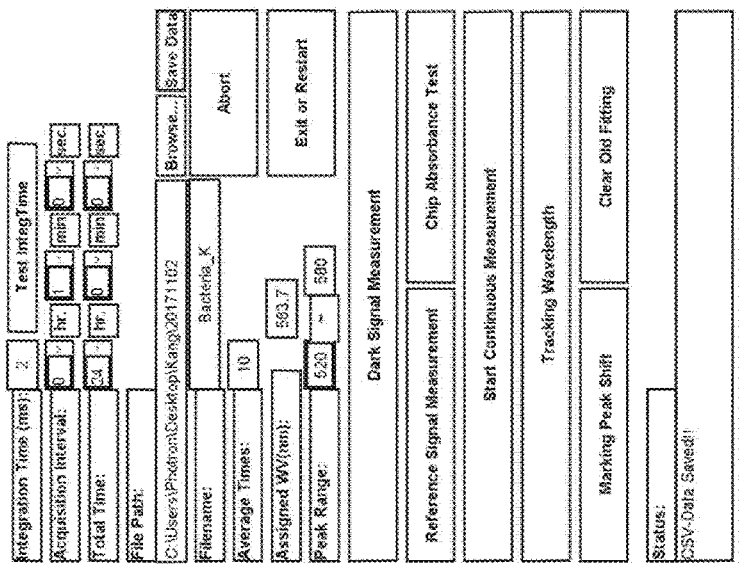

NANOPLASMONIC INSTRUMENTATION, MATERIALS, METHODS AND SYSTEM INTEGRATION

TECHNICAL FIELD

This invention relates to nanoplasmonic instrumentations, materials, methods and system integration.

BACKGROUND ART

As demand for highly sensitive plasmonic nanostructures continues to increase, as does the demand for technologies capable of producing nanostructures at a low cost and high throughput. Current technologies are limited to the micro/nano lithography techniques, which are time consuming and yield structures with limited throughput and low reproducibility (NPL 4).

Nanoplasmonic biosensors allow for highly sensitive label-free detection of biomolecular interactions in real time, an essential feature for the early detection of diseases and point-of-care (POC) clinical evaluations. Nanoplasmonics explore the unique physical and optical properties of noble metal nanostructures associated with a phenomena known as localized surface plasmon resonance (LSPR). LSPR is a coherent oscillation of delocalized electrons and subsequent absorption within the ultraviolet-visible (UV-Vis) band due to interactions between the incident photons and the conduction band of a noble metal nanostructure. Two fundamental approaches are used to develop biocompatible nanoplasmonic materials, top-down fabrication and bottom-up assembly. Essentially, top-down fabrication methods remove building units from a substrate to create nanostructures, while bottom-up assembly physically adds building units to a substrate. Top-down fabrication typically relies on various lithographic methods whereas bottom-up approaches employ molecular synthesis, colloid chemistry, and polymer science to develop structures with nanometer dimensions. Although the inherent nature of bottom-up approaches enables fine resolution, top-down methods are thus far better suited for large-scale, high-throughput nanostructure production. Existing methods from both approaches have enabled great control over the size, shape, and separation of nanostructures; however, materials science still lacks effective means of unifying both approaches to achieve synthesis of highly sensitive nanoplasmonic sensors with high throughput and low cost of fabrication.

Plasma-assisted nanofabrication is an emerging multidisciplinary research area, which offers exciting new niches for the fabrication of a rich diversity of nanomaterials, including nanowires, nanotubes, nanoparticles, and nanotextured coatings. Although nanomaterials developed in plasma environments have remarkable plasma-induced properties that set them apart from their traditional counterparts, it proves to be difficult to fabricate them by using conventional techniques such as standard lithography, e-beam lithography and nanoimprinting (NPL 5, 6). The process of plasma-assisted nanofabrication has many similarities to several processes that occur in nature. Specifically, 99% of matter exists in the plasma state in the cosmic space. For instance, interstellar gas, cometary tails, upper layers of planetary atmospheres and stellar environments, contain plasma environments where sub-nanoscale particles (building units) such as atoms, molecules and ions self-organize into various shapes and configurations.

CITATION LIST

Non Patent Literature

NPL 1: Ostrikov, K. "Colloquium: Reactive plasmas as a versatile nanofabrication tool." Reviews of modern physics 77.2 (2005): 489.

NPL 2: Vladimirov, Sergey V., Kostya Ostrikov, and Alex A. Samarian. *Physics and applications of complex plasmas.* World Scientific, 2005.

NPL 3: Ostrikov, Kostya, Plasma nanoscience: from nature's mastery to deterministic plasma-aided nanofabrication." IEEE transactions on plasma science 35.2 (2007): 127-136.

NPL 4: Hammond, Jules L., et al. "Localized surface plasmon resonance as a biosensing platform for developing countries." *Biosensors* 4.2 (2014): 172-188.

NPL 5: Anker, Jeffrey N., et al. "Biosensing with plasmonic nanosensors." *Nature materials* 7.6 (2008): 442-453.

NPL 6: Willets, Katherine A., and Richard P. Van Duyne. "Localized surface plasmon resonance spectroscopy and sensing." *Annu. Rev. Phys. Chem.* 58 (2007): 267-297.

NPL 7: Kang, Tae Yoon, et al. "Process optimization of CF 4/Ar plasma etching of Au using I-optimal design." Thin Solid Films 517.14 (2009): 3919-3922.

NPL 8: Knizikevičius, Rimantas. "Simulations of Si and $SiO_2$ etching in $SF_6+O_2$ plasma." Vacuum 83.6 (2009): 953-957.

NPL 9: Jia, Kun, et al. "Sensitive localized surface plasmon resonance multiplexing protocols." Analytical chemistry 84.18 (2012): 8020-8027.

NPL 10: Švorcik, V., et al. "Annealing of gold nanostructures sputtered on glass substrate." Applied Physics A 102.3 (2011): 605-610.

NPL 11: Manzano, Marisa, et al. "Development of localized surface plasmon resonance biosensors for the detection of Brettanomyces bruxellensis in wine." Sensors and Actuators B: Chemical 223 (2016): 295-300.

NPL 12: Ou, Y. et al. Broadband antireflection silicon carbide surface by self-assembled nanopatterned reactive-ion etching. *Optical Materials Express* 3, 86-94 (2013).

NPL 13: Kitabayashi, H., Fujii, H. & Ooishi, T., Charging of glass substrate by plasma exposure, Japanese journal of applied physics 38, 2964 (1999).

NPL 14: Becker, J., Tru″gler, A., Jakab, A., Hohenester, U. & So″nnichsen, C. The optimal aspect ratio of gold nanorods for plasmonic bio-sensing. *Plasmonics* 5, 161-167 (2010).

NPL 15: Paivanranta, B. et al., High aspect ratio plasmonic nanostructures for sensing applications, *ACS nano* 5, 6374-6382 (2011).

NPL 16: Parsons, J. et al. Localized surface-plasmon resonances in periodic nondiffracting metallic nanoparticle and nanohole arrays. *Physical Review B* 79, 073412 (2009)

NPL 17: Willets, K. A. & Van Duyne, R. P. Localized surface plasmon resonance spectroscopy and sensing. *Annu. Rev. Phys. Chem.* 58, 267-297 (2007).

NPL 18: Abbas, A., Tian, L., Morrissey, J. J., Kharasch, E. D. & Singamaneni, S. Hot spot-localized artificial antibodies for label-free plasmonic biosensing. *Advanced functional materials* 23, 1789-1797 (2013).

NPL 19: Sepu′lveda, B., Angelome′, P. C., Lechuga, L. M. & Liz-Marza′n, L. M. Lspr-based nanobiosen-sors. *Nano Today* 4, 244-251 (2009).

NPL 20: Wilkinson, C., Riehle, M., Wood, M., Gallagher, J. & Curtis, A. The use of materials patterned on a nano- and micro-metric scale in cellular engineering. Materials Science and Engineering: C 19, 263-269 (2002).

NPL 21: Armbruster, D. A. & Pry, T. Limit of blank, limit of detection and limit of quantitation. Clin Biochem Rev 29, S49-52 (2008).

SUMMARY OF INVENTION

Accordingly, the present invention is directed to nanoplasmonic instrumentations, materials, methods and system integration.

Additional or separate features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, in one aspect, the present invention provides a method for making a plasmonic mushroom array, including: forming a plurality of metal nano-islands each having nanometer-range dimensions on a surface of a glass substrate; and subjecting to the glass substrate having the plurality of metal nano-islands formed thereon to reactive ion etching such that the plurality of metal nano-islands are converted to a plurality of mushroom-shaped structures each having a metal cap supported by a pillar made of a material of the glass substrate and each having dimensions smaller than the dimensions of the nano-islands, the plurality of mushroom-shaped structures being arranged in a substantially regular pattern with intervals smaller than average intervals between the nano-islands, thereby forming the plurality of nano-scale mushroom-shaped structures on the glass substrate that can exhibit localized surface plasmon resonance.

In another aspect, the present invention provides a plasmonic plate, including: a glass substrate; and a plurality of mushroom-shaped structures on the glass substrate each having a metal cap supported by a pillar made of a material of the glass substrate and each having nano-scale dimensions, the plurality of mushroom-shaped structures being arranged in a substantially regular pattern so as to exhibit localized surface plasmon resonance.

In another aspect, the present invention provides a localized surface plasmon resonance device, including: an LED circuit including a light emitting diode emitting light downwardly; a plasmonic chip disposed under the LED circuit, the plasmonic chip including the plasmonic plate as set forth above, and facing the light emitting diode to receive light from the light emitting diode; a fluid stage disposed under the LED circuit such that a fluid provided in the fluid stage can operably couple with the plasmonic plate; and a spectrometer disposed under the plasmonic chip to receive light that has interacted with the plasmonic plate so as to analyze spectrum of the received light.

It is to be understood that both the foregoing general description and the following detailed description are exemplary and explanatory, and are intended to provide further explanation of the invention as claimed.

BRIEF DESCRIPTION OF DRAWINGS

FIG. 1 schematically illustrates a plasma process fabricating Au nanomushroom (NMs) structures from Au nanoislands (NIs). a): Scanning electron microscopy (SEM) image alongside schematic representation of NIs. The inset shows zoomed in picture of NIs. b): schematic drawing of NIs under plasma exposure. c): NMs formed after plasma exposure to plasma. The inset shows cross section of the NMs.

FIG. 2 schematically illustrates a process of fabrication for nanomushroom like structures (NMs). Schematics show the generation of building units (BUs) from nanoislands (NIs), and subsequent assembly of BUs into more tightly packed NMs.

FIG. 3 schematically illustrates the concept of the building units (BUs) as applied to the present invention.

FIG. 4 is a photograph of NIs having a 200 nm diameter with the spacing of 100 nm, which were made using e-beam lithography (EBL).

FIG. 5 is a photograph of the structure after performing ICP-RIE treatment on the NI structure shown in FIG. 4.

FIG. 6 is a process flow chart of an NM manufacturing process according to an embodiment of the present invention.

FIG. 7 schematically shows a process to achieve a high throughput NM structure according to an embodiment of the present invention.

FIG. 8 schematically shows the dimensions and spacing of the NM structure according to an embodiment of the present invention.

FIG. 9(a) is an absorbance plot as a function of wavelength for the NIs and the NMs, and shows typical resonance characteristics of NIs (the LSPR peak wavelength of 540 nm) and NMs (the LSPR peak wavelength of 533 nm) structures.

FIG. 9(b) shows the changes in the LSPR peak wavelengths of the respective NM and NI structures with changes in local refractive index around them.

FIG. 10 is a drawing that schematically demonstrate cell proliferation (NIH/3T3 fibroblasts) on a NM substrate of the present invention.

FIGS. 11(a) to 11(h) show LSPR of a Working Example NM structure of the present invention upon proliferation of cells: FIG. 11(a) shows wavelength response over 24 hrs.; FIG. 11(b) shows absorption response over 24 hrs.; FIG. 11(c) shows RIU response over 24 hrs; FIGS. 11(d) to 11(f) show LSPR upon proliferation of cells over 7 days, wherein FIG. 11(d) show wavelength response; FIG. 11(e) shows absorption response; and FIG. 11(f) shows MU response; FIG. 11(g) shows images of the surface of NM sensor after each day; and FIG. 11(h) shows changes in cell number vs changes in sensor response.

FIG. 12 is a photograph showing a stencil hard mask made with Aluminium made by using CNC machines.

FIG. 13 schematically illustrates deposition of gold in spots using the mask of FIG. 12.

FIG. 14 is a photograph showing a NM chip having an array of nanomushrooms spots manufactured according to a Working Example of the present invention.

FIG. 15 is a photograph showing the packaged nanomushroom chip with microchannels that was manufactured according to an embodiment of the present invention.

FIG. 16 shows mechanism of fabrication for nanomushroom like structures (NMs): a) schematically shows generation of building units (BUs) from nanoislands (NIs), and subsequent assembly of BUs into more tightly packed NMs; b) shows preferred size and pitch requirements for plasma directed assembly of NMs from NIs; c) to e) are scanning electron microscopy (SEM) images of plasma effects on NIs; c): 200 nm diameter, pitch 200 nm; d): 200 nm diameter, pitch 100 nm; e): size 100 nm pitch 100 nm.

FIGS. 17(a) to 17(m) show configuration and results of verification experiments: FIG. 17(a) schematic of plasma shield for creating gradient of ions; FIGS. 17(b) to 17(g) SEM scans of areas under stamp, from FIGS. 17(b) to 17(g) with increasing exposure to intensities of plasma ions. Inside each image, inset shows the size distribution of nanostructures; FIGS. 17(h) and 17(i) nanoislands created using E-beam lithography; FIGS. 17(j) and 17(k) nanoislands after exposure to 1 min of plasma; and FIGS. 17(l) and 17(m) nanoislands after exposure to 5 min of plasma.

FIG. 18(a) shows characteristics of LSPR peaks. The inset shows sensitivity of the LSPR peak of the NI, NM structures to changes in refractive index.

FIGS. 18(b) to FIGS. 18(e) show micro contact printed antibody on NMs: FIG. 18(b) micro contact printed antibody on NM; FIG. 18(c) microcontact printed antibody on NI; FIG. 18(d) micro contact printed antibody in complex shapes such OIST logo; and FIG. 18(e) in ability of NI to print antibody in complex shapes.

FIG. 18(f) shows LSPR response to binding of complementary antibody on micro contact printed antibody.

FIGS. 18(g) and 18(h) show dose response of LSPR showing changes in wavelength and absorption upon attachment of complementary antibodies of varied concentrations.

FIG. 19 shows the main components of an LSPR sensor device having the mushroom LSPR chip according to an embodiment of the present invention.

FIG. 20 is the circuit diagram for the LED circuit of the LSPR sensor device shown in FIG. 19.

FIGS. 21 to 23 are various views of the light source panel included in the LSPR sensor device embodiment shown in FIG. 19, including several side views, top and bottom views, and front and back views.

FIG. 24 is a block diagram of the spectrometer module in the LSPR sensor device embodiment shown in FIG. 19.

FIGS. 25(a) to 25(c) show the design drawings of the Fluid Stage in the LSPR sensor device embodiment shown in FIG. 19: FIG. 25(a) bird view of fluidic channel; FIG. 25(b) side view of fluidic channel integrated in LSPR system and enlarged view thereof; and FIG. 25(c) the top and cross-sectional views of the fluidic channel.

FIGS. 26(a) to 26(c) FIG. 26(a) schematically shows stage holder attached to the light source panel, FIG. 26(b) schematically shows the donut shaped pressurizer and FIG. 26(c) schematically shows a detachable key for attaching pressurizer on the stage in the LSPR sensor device embodiment shown in FIG. 19.

FIG. 27 shows a flowchart of all steps involved in readout and displaying the signals from the spectrometer in the LSPR sensor device embodiment shown in FIG. 19.

FIG. 28 shows a graphics user interface developed in Matlab to display the LSPR signal in real time in the LSPR sensor device embodiment shown in FIG. 19.

DESCRIPTION OF EMBODIMENTS

Inspired by the nature's nanofabrication process, this disclosure presents a highly effective and easy-to-manufacture new plasmonic structure of a metal-topped mushroom like nanostructure that is usable as an LSPR element, and demonstrates a simple, laboratory-based method for the formation of the metal-topped mushroom like nanostructures inside a plasma environment of sulfur hexafluoride ($SF_6$), as shown in FIG. 1. Briefly, in one embodiment, a silicon dioxide ($SiO_2$) substrate with heterogeneous distribution gold (Au) nanoislands (NIs) was exposed to a plasma of sulfur hexafluoride ($SF_6$). The Au NIs was prepared by dewetting of a thin gold film (of 4 nm thick) on glass. Ions of $SF_6$ selectively etch $SiO_2$, while Au NIs serve as nanomasks for the underlying $SiO_2$. This resulted in the formation of a novel structure of an Au nanomushroom structures (NMs), where each nanostructure is made of a $SiO_2$ stem with a cap of Au.

FIG. 1 schematically illustrates a plasma process fabricating Au nanomushroom (NMs) structures from Au nanoislands (NIs). a): Scanning electron microscopy (SEM) image alongside schematic representation of NIs. The inset shows zoomed in picture of NIs. b): schematic drawing of NIs under plasma exposure. c): NMs formed after plasma exposure to plasma. The inset shows cross section of the NMs.

As shown in FIG. 1, an intriguing surface redistribution of gold nanostructures was observed during the formation of NMs. The NMs were found to be more homogenous in comparison to NI structures after ICP-RIE (inductive coupled plasma-reactive ion etching) treatment. Experimental evidence is provided below to reveal how the plasma environment contributes to the re-distribution of gold upon ICP-RIE process, resulting this novel fine structure. As explained below, this novel structure has highly sensitive plasmonic characteristics and is usable for various applications utilizing LSPR. But first, the mechanism for creating this novel nanostructure is discussed.

Au Nanostructure Re-Distribution Mechanism

To investigate the mechanism for this surprising finding, Au NIs are created by depositing a nanolayer of Au onto a $SiO_2$ surface by electron beam vapor (e-beam) deposition, after which the structures are annealed at 560° C. for 3 hours. The Au NIs then undergo reactive ion etching (ICP-RIE) in a $SF_6$ plasma environment, with Au NIs serving as nanomasks for the $SiO_2$ substrate. $SF_6$ etches $SiO_2$ at a much faster rate than Au, allowing the formation of NMs as the $SiO_2$ around each NI is removed. $SF_6$ etching of $SiO_2$ is a chemical process, where $SiO_2$ is dissolved in the plasma environment, while Au is etched from the surface by a physical process. These physically etched Au particles (in the form of atoms, clusters of atoms and molecules of Au) are non-volatile in nature, thus available to serve as building units (BUs) for further assembly on etched $SiO_2$ surfaces (NPL 7). In contrast, the product of chemical etching of $SiO_2$ is oxysilicon-fluorine, which vaporizes in the plasma environment (NPL 7). This distribution of Au BUs is attributed to: 1) the charging of the $SiO_2$ substrate inside the plasma environment; and 2) the interaction of plasma flux with the spatial distribution of NI masks. Plasma of fluorine is highly electronegative in nature, inducing a positive charge on the surface of $SiO_2$. The interactions between surface charges and fluorine ions in the $SF_6$ plasma environment, in turn attract the Au BUs onto the substrates surface. These newly deposited BUs accumulate to form new, smaller NIs, while the etching process continues. As shown in FIG. 1, the final distribution of NMs is thus more tightly packed than the original NI distribution. A schematic explanation of the process in shown in FIG. 2. FIG. 2 schematically illustrates a process of fabrication for nanomushroom like structures (NMs). Schematics show the generation of building units (BUs) from nanoislands (NIs), and subsequent assembly of BUs into more tightly packed NMs.

The building units (BUs) explained above refer to the tiny pieces of gold (single atom, cluster of atoms, nucleates agglomerates of gold) which sputter out from Au nanoislands (NIs) when they are placed inside the plasma environment. This generation and redistribution of building units of gold on the glass surface is attributed to the interaction of plasma with the material gold. The concept of building units can be understood in more detail from Ostrikov's work on FIG. 3 and NPL 1-3. FIG. 3 is a picture reprinted from NPL 3.

Since the distribution of gold in our original nanoisland substrate is random, it is difficult to verify the BU effect clearly from an initially randomly arranged structure. Therefore, for the purpose of the investigation, we first used e-beam lithography (EBL) to create a substrate containing nanostructures of controlled size and distribution (ordered structures), as shown in FIG. 4. FIG. 4 is a photograph of NIs having a 200 nm diameter with the spacing of 100 nm, which were made using e-beam lithography (EBL).

After ICP-RIE treatment of the NIs, tiny nanomushrooms are observed in between the bigger nanomushrooms structures. FIG. 5 are photographs of the structure after performing ICP-RIE treatment on the NI structure shown in FIG. 4. As shown in FIG. 5, the NM structure is observed. These tiny nanomushrooms are formed by physical sputtering of gold from nanoislands in the plasma environment, which verifies our building block theory explained above.

Manufacturing Method

Embodiments of the present invention can be manufactured generally as follows.

Step 1: Forming metal-topped nanoislands (NIs) on a glass substrate. A preferred metal is gold. These NIs are precursors of NMs. The Nis may be created by various methods such as the standard lithography, e-beam lithography or dewetting. However, as described in detail below, dewetting may be preferable because of its simplicity and economy.

Step 2: Exposing the glass substrate in step 1 above to IC-ICP-RIE and creating nanomushrooms (NMs) on the glass substrate. The exact dimension of the substrate size (containing NMs) is limited by the size of the e-beam evaporator that treats the substrate in the case of using the e-beam evaporator. The e-beam evaporator used in making working examples of the present invention allowed us to create a sample (glass substrate with NMs) of a length of 25 mm and width of 75 mm.

The flow chart in FIG. 6 shows steps of the manufacture process of this embodiment. FIG. 7 illustrates the main steps of the fabrication process according to one embodiment of the present invention. It is believed that the NMs each made of a glass stem and a gold top (see FIG. 8) created from the NI substrate is new and is never achieved before. FIG. 6 is a process flow chart of an NM manufacturing process. As shown in FIG. 6, in this embodiment, NIs made of gold is fabricated by dewetting or e-beam lithography or standard photolithography. For large scale high throughput production of gold NIs on a glass substrate, dewetting—i.e., deposition of a gold layer followed by annealing to create NIs—is preferable.

The gold NIs on the glass substrate is then subject to the inductive coupled reactive ion etching (ICP-RIE) so as to create nanomushrooms (NMs) on the glass substrate, each being made of a glass stem and a gold top (FIG. 8).

FIG. 7 schematically shows a process to achieve a high throughput NM structure according to an embodiment of the present invention. As shown in FIG. 7, a glass substrate is first prepared, and a gold layer is deposited on the glass substrate. Annealing of the gold deposited substrate is performed to create a plurality of nanoislands (NIs) on the substrate, each made of gold by dewetting. Then, the resulting substrate is subject to the RIE to create a plurality of finer and smaller nanomushrooms (NMs).

Working Examples

In the case of using dewetting in creating gold NIs, it is possible to create gold nanoislands under different manufacturing conditions, by varying the thickness of Au layer, annealing temperature and the time of annealing, for example (NPL 5-7). Preferred process parameters for working examples of the present invention are listed in Table 1 below.

TABLE 1

| Thickness of Au | Annealing Temperature | Annealing Time |
| --- | --- | --- |
| 4 nm | 560° C. | 3 hrs |

A working example was manufactured using the following steps.

Step 1: Deposit 4 nm of gold (Au) layer on a glass/$SiO_2$ substrate using e-beam vapor deposition technique. (Note: Au can be deposited by any standard metal deposition method such as thermal evaporation of metal, chemical vapor deposition or magnetron sputtering process.)

Step 2: Anneal Au on glass in a hot furnace at 560° C. for 3 hours to form Au NIs.

Step 3: Perform reactive ion etching of Au NIs using $SF_6$ gas, 5° C., 10 W/150 W power for 5 minutes. As a result, gold nanoislands (Au NIs) transformed into nanomushrooms (Au NMs).

FIG. 8 schematically shows the dimensions and spacing of the NM structures fabricated in the above-described conditions, which is a Working Example of the present invention. Each NM consists of an Au cap and a $SiO_2$ stem. Table 2 below lists the dimensions measured in this Working Example in more detail.

TABLE 2

|  | Au Cap diameter (nm) | Total thickness (nm) | Average cap diameter (nm) | Spacing range (nm) | Average Spacing (nm) |
| --- | --- | --- | --- | --- | --- |
| Nanoislands | 5-70 | 20-25 | 35 | 2-80 | 25 |
| Nano-mushrooms | 10-30 | 45-60 total Au (15-20) $SiO_2$ (30-40) | 25 | 5-20 | 10 |

As shown in FIG. 8 and the Table above, each mushroom structure has an Au cap with the diameter of 10-30 nm and has the height of 45-60 nm among which the Au height is 15-20 nm and the $SiO_2$ height is 30-40 nm, and the spacing between the mushroom structures is 10 nm on average, which is much finer than the staring NI structure. As compared with the existing materials, the resulting new fine nanostructure of NMs of this Working Example possesses superior plasmonic characteristics, as will be described below Evaluation of Embodiment/Working Example LSPR Sensing Performance of NMs FIG. 9(a) is an absorbance plot as a function of wavelength for the NIs and the NMs. It shows typical resonance characteristics of NIs (the LSPR peak wavelength of 540 nm) and NMs (the LSPR peak wavelength of 533 nm) structures. In general, decreasing the aspect ratio (width/height) of nanostructures results in blue shifts in the peak wavelength due to LSPR (i.e., the LSPR peak wavelength). Therefore, an average blue shift of 7 nm in the NM structures is attributed to the smaller size of NMs (10-30 nm) as compared to NIs (5-70 nm).

FIG. 9(b) shows the changes in the LSPR peak wavelengths of the respective NM and NI structures with changes in local refractive index around them. The refractive index of the sensor was characterized using water, acetone, isopropanol and ethanol. The slope of the line provides the sensitivity of the respective nanostructures and it is observed that the NMs according to the Working Example of the present invention are 4 times as sensitive (80.2 nm/RIU) as the NIs (21.1 nm/RIU). The increased periodicity due to quasi-homogeneous distribution of NMs is primarily responsible for the enhancement in sensitivity of the NM structures. Furthermore, the tips of NMs are much smaller than NIs. Smaller nanostructure features give rise to hot-spots in the electromagnetic field that increase the sensitivity to changes in local refractive index and amplify surface-enhanced phenomena such as LSPR.

Applications and Working Examples of the NM Structure

Various applications of the NM structure of the present invention are contemplated. The above-described basic LSPR characteristics of the NM structure are further confirmed and the applications therefor are also demonstrated below in several ways.

Detection of Cell Proliferations

FIG. 10 schematically demonstrates the cell proliferation (NIH/3T3 fibroblasts) experiment/demonstration conducted on a NM substrate according to a Working Example of the present invention.

The NM substrates, each of which were manufactured as described above, were placed into 35 mm (9 cm') corning cell-culture dishes. The NMs were sterilized using isopropanol, 70% ethanol, and finally allowed to dry in the cell-culture biosafety cabinet under UV light. PDL solution was made at 0.003% in PBS, for a volume of 5001 per NM substrate. Devices were coated with the PDL solution and placed into the cell-culture incubator, a humidified environment at 375° C. with 5% $CO_2$, for 30 minutes. Dishes were then pre-filled with 1 mL of Dulbecco's Modified Eagle Medium high glucose (DMEM) supplemented with 10% calf-serum. Here we use NIH/3T3 fibroblasts as for our cell study. NIH/3T3 fibroblasts were then seeded in the dish at low densities (approximately 0.2×106 cells per dish). Cell culture media was then added to make the final volume 2 mL. An LSPR reading was made immediately. Cells were then allowed to grow in the cell-culture incubator for the indicated amount of time. No new cell-culture medium was added or removed from the dish for the duration of the experiment. For cell-number experiments, the Au NM devices were washed with 1×PBS two times after taking an LSPR measurement. After this, 1 mL of trypsin was added to strip cells. The number of cells were counted using a hematocytometer.

FIGS. 11(a) to 11(h) show LSPR response of a NM plasmonic sensor upon proliferation of fibroblast cells. FIG. 11(a) shows the changes in the wavelength of LSPR in the NMs during the first 24 hours of the experiment. As cells begin to divide, the LSPR peak of NMs shifts linearly towards the left (blueshift) side of the UV-visible spectrum for 15 hours. A change of 2-3 nm is observed during first 15 hours, after which the LSPR signal stabilizes for the next 6-8 hours. These shifts are attributed to 1) increase in the number of cells upon onset of proliferation and 2) adsorption of proteins and other growth factors secreted by the cells. The masking of the NMs by initial changes in the proliferation of cells is primarily responsible for the stabilization of the LSPR wavelength response after 15 hours. FIG. 11(b) shows the absorption intensity of the LSPR. The NM surface is continuously masked by cell growth and secretion, leading to a fall in the intensity of absorption of NMs as the intensity of incident light that reaches NMs decreases. The wavelength changes were translated into refractive index change in FIG. 11(c). A maximum change of 25-30 mRIU (milli refractive index unit) is observed upon proliferation of cells during the first 24 hours, as shown in FIG. 11(c). FIGS. 11(d)-11(f) respectively show the wavelength, absorption intensity, and refractive index change responses of LSPR, over a period of 7 days. Interestingly, the wavelength peak of LSPR after 1 day shifts towards the right side of the UV-vis spectrum (redshift), resulting in a fall in wavelength change response in the graph of changes in blueshift, as shown in FIG. 11(d). While changes in the wavelength response is observed, there is less than 0.1 unit change in the intensity of LSPR absorption, as shown in FIG. 11(e). Since the frequency is inversely proportional to the wavelength, the overall observation of changes in the LSPR peak shifts can be simplified in terms of frequency change of LSPR. During the initial stages of cell proliferation (less than 15 hours), the increase in cell secretions and the number of cells on NMs elevates the optical extinction coefficient of NMs at the resonant frequency. This leads to confinement and concentration of electromagnetic energy in the form of dielectric fields on the surface of the NM structures. Henceforth, an increase in the frequency of the LSPR, i.e. a decrease in wavelength (blueshift), is observed in the LSPR peak. However, with continued increase in the number of cells over a period of 7 days, charge localization effects (the build-up of surface charges on the NMs due to increased cell number) decreases the frequency of the LSPR, and increases the wavelength (redshift). FIG. 11(g) shows images of the cells on the NMs over 7 days during the proliferation experiment. This figure indeed shows cell proliferation properly detected by the Working Example of the present invention.

The wavelength response of LSPR was also quantified for the number of cells on the surface. As shown in FIG. 11(h), it was observed that the LSPR response varies linearly with increase in the number of cells. With a fewer cells, blueshift is observed, while an increase in number of cells corresponds to the observation of redshifts in the LSPR peak. Therefore, it is possible for a practical LSPR cell proliferation biosensor to be calibrated with a range of wavelengths against a variety of numbers of cells.

NM LSPR Chip

To use the nanomushrooms (NMs) of embodiments of the present invention for any generic bioassay application, it is important to make assay plates of nanostructures such as the 96 well standard ELISA plates. The above-described 2 step (dewetting and ICP-RIE) NM manufacturing process allows us to make plasmonic spots consisting over a million nanomushrooms structures. Each spot is like an individual well of a standard ELSIA plate. To create it, a stencil (hard mask) may be used to create spots of nanomushrooms from predefined array formats. First, the hard mask shown in FIG. 12 is placed on a glass substrate during the evaporation of gold, as shown in FIG. 13. Then Annealing is performed on the Au layer formed on the glass substrate in hot oven furnace at 560° C. for 3 hours to form Au NIs. Subsequently, reactive ion etching (RIE) of the NIs is performed by using $SF_6$ gas, 5° C., 10 W/150 W power for 5 minutes. As a result, gold nanoislands (Au NIs) transform into nanomushrooms (Au NMs).

FIG. 14 shows the developed spotted plasmonic chip that was manufactured this day. Each spot has over $10^6$ to $10^7$ nanomushrooms and each spot can be used for a single assay. The spot diameter was 3 mm, however it is possible to change the size of the spot as per the need of the user. This can be done by adjusting the size of the hard mask. In addition, the mask is re-usable.

Packaging the NM Plasmonic Chip: Microchannels on Nanomushroom

Packaging nanomushrooms chip allows precise fluid handling on the developed spots. The NM structures of the present invention was integrated with microchannels. FIG.

15 is a photograph showing the packaged nanomushroom chip with microchannels that was manufactured according to an embodiment of the present invention. The method to package the chip involves the following steps.

1) A standard soft-lithography protocol is used to fabricate a silicon master. Microchannels are designed using AutoCAD. The glass slide is spin coated with a negative photoresist (mr-DWL, Micro resist technology) with 1050 RPM for 30 seconds to fabricate the master with the thickness of 100 μm.

2) The master is pre-baked on a hotplate at 50° C. for 5 min and at 80° C. for 30 min.

3) The master is exposed under LED light by using a maskless lithography system (Dlight DL-1000, Nanosystem solutions) with the intensity of 500 mJ/cm². Then the master is soft-baked on a hotplate at 50° C. for 5 min and at 80° C. for 30 min.

4) The master is developed with a photoresist developer for 5 min, followed by hard-bake on a hotplate at 50° C. for 5 min and at 80° C. for 30 min.

<Microchannel Fabrication>

1) The base and curing agents of PDMS with 10:1 mixing ratio (Sylgard 184, DowCorning) was poured onto the silicon master, degassed in a vacuum desiccator, and cured in an oven at 70° C. for 6 hours.

2) The PDMS device is cut from the master, and punched with a sharpened flat-tip needle to make inlets and outlets.

3) The PDMS device and slide glass with gold nanoislands are treated with oxygen plasma for 40 seconds, followed by bonding between them securely by hand.

4) The device is placed onto a hotplate at 120° C. for 20 min to increase the bonding strength.

As described above, the present disclosure provides a method for making metal-top nanomushroom structures on a glass substrates as large as 25 mm in width and 75 mm in length. The process is a high throughput NM production process. The resulting metal-top nanomushroom structures are new and highly effective in creating highly sensitive and biocompatible LSPR sensors. The enhanced sensitivity and enhanced biocompatibility are particularly useful for living cells survival. This gives rise to new opportunities to develop LSPR sensing for a large number of unexplored applications in cell biology, for example.

Various applications of the novel NM structure are disclosed, including a multiplexed LSPR chip having a plurality of NM spots, an integrated NM chip with microfluidics. Table 3 below summarize various advantages of the present invention over the existing technologies.

Additional Details of Embodiments of Invention

Certain additional details of the disclosure described above are provided below. Some of the descriptions below overlap with the descriptions provided above.

Reactive Ion Etching (RIE) described above may be performed at a temperature of 5° C. with an $SF_6$ flow rate of 45 sccm, the Ion steering power of 10 W and the power intensity of 150 W to suitable form the NMs.

Surprising result of quasi periodic structure resulting from quasi-random islands: As described above, the transition from Au quasi random islands to Au nano mushroom quasi periodic structures is facilitated by using $SF_6$ plasma with the proper operation conditions. The electronegative $SF_6$ plasma is a well-known etchant for $SiO_2$. However, during the etching of $SiO_2$, Au also gets etched in the plasma environment, but with a much slower etching rate. $SiO_2$ etches out at a rate of 10 nm/min (layer thickness) as compared to less than 1-2 angstrom/min of Au etching (i.e., $SiO_2$ is etched away at least 100 times faster than that of Au) (NPL 8). If the size and the gap size of nanoislands (NI) are less than 100 nm, redistribution of Au on $SiO_2$ surface is observed from systematic experiments. This result indicates that the preferred and perhaps critical size and gap size of NI required for the NM formation are both about 100 nm.

In determining the distribution and average of the size and spacing dimension of the NIs and NMs described above— i.e., in performing surface distribution analysis of these nanostructures FFT (Fast Fourier Transform) profile plot analysis was used using Image J software.

The criticality of process parameters to creating nanoislands (NI): As described above, it is possible to create Au NIs with different size and spacing by varying manufacturing conditions, e.g., initial Au thickness, annealing temperature and the time of annealing. This has been reported in literature (NPL 9-11). Based on the extensive studies conducted by the inventors, Au NIs with average size and spacing less than 100 nm are preferred for the NM formation with the subsequent proper plasma etching step. An example of preferred process parameters to create desirable NIs are as described above: i.e., the thickness of Au: 4 nm, the Annealing Temperature of 560° C., and the Annealing Time of 3 hrs.

<Evaluation of Plasma Assisted Nanomushroom Fabrication>

To further investigate the plasma assisted fabrication of nanomushrooms, Au NIs are formed using electron beam vapor deposition, depositing a nanolayer of Au onto a $SiO_2$ surface and annealing at 560° C. for 5 hours. During subsequent RIE in a $SF_6$ plasma environment, these Au NIs serve as nanomasks for the $SiO_2$ substrate. $SF_6$ etches $SiO_2$

TABLE 3

|  | Throughput | Production speed for 1 spot of 3 mm | Area dependency | Stability | Cost | Multiplex chips |
|---|---|---|---|---|---|---|
| Nanoscale lithography | Medium | 24 hrs | Y | Poor to Good | $$ | Y |
| E-beam lithography | Low | 1 week | Y | Good | $$$$ | N |
| Chemical synthesis | Medium | 48 hrs | Y | poor | $$ | Y |
| Present Invention | High | 3.5 hrs | N | Good | $ | Y | much faster than Au (NPL 12), allowing the formation of NMs as the $SiO_2$ around each NI is removed. The $SF_6$ etching ejects sub-nanometer particles of $SiO_2$ and Au from the surface. These particles are thus available to serve as building units (BUs) in nanoassembly. This assembly is facilitated by the fact that $SiO_2$ BUs are ejected from the substrate, while Au BUs are instead redistributed on the surface to form new NMs. Au BU redistribution is attributed to 1) the charging of the $SiO_2$ substrate inside the plasma environment (NPL 13) and 2) the interaction of plasma flux with the spatial distribution of NI masks. Plasma of fluorine is highly electronegative in nature, inducing a positive charge on the surface of $SiO_2$. The interactions between surface charges and fluorine ions in the $SF_6$ plasma environment push Au BUs back down onto the substrates surface. These newly deposited BUs accumulate to form new, smaller NIs, and etching continues. As shown in FIG. 16, the final distribution of NMs is thus more tightly packed than the original NI distribution.

FIG. 16 show mechanism of fabrication for nanomushroom like structures (NMs): a) schematically shows generation of building units (BUs) from nanoislands (NIs), and subsequent assembly of BUs into more tightly packed NMs; b) shows preferred size and pitch requirements for plasma directed assembly of NMs from NIs; c)-e) are scanning electron microscopy (SEM) images of plasma effects on NIs; c): 200 nm diameter, pitch 200 nm; d): 200 nm diameter, pitch 100 nm; e): size 100 nm pitch 100 nm.

The spatial distribution of NI masks also interferes with the flux of plasma, changing the etch rate. In order to assess the role of NI size and spacing (pitch) on plasma directed reorganization of metals, three sets (set 1: 200 nm diameter, pitch 200 nm, FIG. 16(c) set 2: 200 nm diameter, pitch 100 nm, FIG. 16(d), set 3: size 100 nm pitch 100 nm, FIG. 16(e) of uniformly sized NI grids were fabricated using electron beam lithography (EBL).

It is observed that disorder increases during etching, due to the redeposition and reorganization of particles as the size of NIs decreases. From set 3 in FIG. 16(e), it can be observed that Au NIs start re-orienting (transition stage) and upon completion of the fabrication process, the distribution of NMs is disordered, in comparison to its precursor NIs. However, if we consider heterogeneously distributed NIs fabricated using dewetting, as described above, the distribution ultimately becomes quasi homogeneous upon formation of NMs, as gaps between NIs are filled with new structures. Therefore, as the size and spacing on NIs decrease, etching-induced disorder increases. Based on these observations, it is preferable, as shown in FIG. 16(b), that redistribution and re-organisation of Au may be driven by plasma only when the feature size of NIs and the pitch between them are both less than 100 nm.

<Plasma Assisted Reorganization of Metal>

To confirm that the reorganisation of metal was driven by plasma, two experiments were conducted. In the first experiment, we developed a rubber shield to create a gradient of plasma as shown in FIG. 17(a). The shield generates a gradient of reactive ions on the substrate's surface during plasma treatment. The highest concentration of ions is at the entrance of the shield and the lowest is at the end of the shield. This gradient of reactive ions produces a gradient of plasma, thereby exposing the surface of NIs to a gradient of etching rates. It was observed that the shield also slows down the etching rate of $SiO_2$ from glass and, as a result, NMs are not visible. This decrease in etch rate is primarily due to the plasma's loss of energy after reactive ions enter the shielded region. Interestingly, we notice that the reorganisation properties of the plasma were not lost, as evident from observed differences in the distribution of Au under different regions of the plasma shield. Thus, these gradients allow us to capture some of the re-organizational properties of plasma responsible for the formation of NMs from NIs. FIGS. 17(b)-(g) show different regions of a NI substrate under a shield exposed to plasma for 5 minutes, ordered from lowest to highest concentration of reactive ions. It was observed that re-distribution of Au in the areas which were exposed to a higher concentration of reactive ions, as shown in FIGS. 17(e) and (f). Surprisingly, the redistribution of Au in these regions resulted in its homogeneous distribution on the surface. The Au structures in FIGS. 17(e) and 17(f) have a distinct shape, in comparison to the heterogeneous NI distribution seen in FIGS. 17(b)-(d). FIG. 17(g) shows the region of NIs at the entrance of the shield. In this area, no shield, and the consequently unreduced $SiO_2$ etch rate, results in over etching of the substrate for this duration of plasma exposure. Such over etching implies that if the areas shown in FIG. 17(f) are etched longer, then some structures of Au would be fully ejected, re-depositing to form coarsely distributed larger structures. Moreover, the mass of Au in a given area is conserved during the assembly of new structures. FIG. 17(h) plots the total area of Au in the images on FIGS. 17(b)-(g). The slight differences in each region are attributed to the heterogeneous distribution of NIs, which varies the amounts of Au present in each surface region prior to plasma exposure. These results support the process of BU generation and transport towards self assembly, as described above.

A second experiment was conducted to observe mass conservation during plasma reorganization in more detail. In this experiment, ordered Au NIs of size 100 nm and pitch 100 nm were fabricated on a silicon (Si) substrate using electron beam lithography (EBL), as shown in FIG. 17(i). The adhesion of Au on Si is weak, and upon exposure to plasma, we expect Au NIs to peel off the substrate, generating a blank Si surface. While NIs do peel off from their initial deposition point, they remain confined to the total area of deposition, as shown in FIGS. 17(j)-17(m), supporting strong re-organizational properties of plasma on Au NIs.

Furthermore, when the etching is prolonged over 5 min, the NIs still remain enclosed within the total area where they were initially deposited. Instead of removal, plasma re-organisation of NIs leads to the nanoassembly of short Au NI chains, resembling protein structures. As seen from FIG. 17(i), extended plasma exposure further squeezes NIs into more rigid protein-like chains. The continued formation of these chains further establishes experimental evidence of our claim that plasma assists in the reorganisation of metal. These properties of plasma re-organization are primarily responsible for the quasi-homogeneous distribution of NMs in comparison to precursor NIs.

<Micro Contact Printing and Bioassay>

FIG. 18(a) shows typical resonance characteristics of the NI (540 nm) and NM (533 nm) structures, respectively. In general, decreasing the aspect ratio (width/height) of nanostructures results in blue shifts in the wavelength of LSPR (NPL 14, 15). Therefore, an average blue shift of 7 nm in NM structures is attributed to the smaller size of NMs as compared to NIs. The inset on FIG. 18(a) shows the changes in wavelength of the NM and NI structures with change in local refractive index around them. The refractive index of the sensor was characterized using water, acetone, isopropanol and ethanol. The slope of the line provides the sensitivity of the nanostructures and it is observed that the NMs are 4 times as sensitive (80.2 nm/RIU) as NIs (21.1 nm/RIU). The increased periodicity due to quasi homogeneous distribution of NMs is primarily responsible for the enhancement in sensitivity of the NM structures (NPL 16). Furthermore, the tips of NMs are much sharper than NIs. The sharp nanostructure features give rise to hot-spots in the electromagnetic field that increase the sensitivity to changes in local refractive index and amplify surface-enhanced phenomena such as LSPR (NPL 17-19).

To validate the use of NMs for binding studies, we detected selective binding of complementary pairs of antibodies. The antibodies were immobilised on the nanostructures (NMs and NIs) using micro contact printing (CP). Subsequently, the complementary antibody pair was specifically attached. FIGS. 18(*b*) and 18(*c*) show printing of antibodies on NMs (FIG. 18(*b*)) and NIs (FIG. 18(*c*)). It was observed that the printing of antibodies on NMs is more uniform and homogeneous than on NIs, demonstrating that the surface of NM distributions is flat and homogeneous in comparison to that of NIs. Moreover, patterning surfaces with proteins in complex shapes is useful in creating micro/nano environments of cells NPL 20). FIGS. 18(*d*) and 18(*e*) show a complex pattern (OIST logo) of proteins successfully printed on NMs (FIG. 18(*d*)), as compared with incomplete printing due to the rough surface morphology of NIs (FIG. 18(*e*)). These results stress the utility of plasma assembled NMs as nanostructures that are superior to their precursor NIs for sensing and for the pattering of nanoscale surfaces with biomolecules. FIG. 18(*f*) shows a concentration dependent LSPR dose-response, with 10 ag/ml to 1000 ng/ml binding of complementary antibody. In FIGS. 18(*g*) and 18(*h*), LSPR response (changes in wavelength, FIG. 18(*g*), and absorbance intensity, FIG. 18(*h*)) for 1) the specific binding of antibody to its complementary pair patterned on NMs and 2) the adsorption of complementary antibody on blank NM surfaces (without patterned antibodies) is plotted. A standard bioassay response (S-shaped) is observed against varied concentrations of secondary antibody in both wavelength and absorbance intensity of the LSPR signal. Upon attachment of 10 ag/ml of complementary antibody on the patterned NM surface, an average LSPR red shift of 5 nm and a less than 0.1 unit of change in absorbance intensity is observed. The LSPR response shows less than 2 nm and 0.1 U change upon further addition of antibodies up to a concentration of 100 fm/ml. Above 100 fm/ml a linear response in the LSPR signal is observed upon addition of antibody concentrations ranging from 100 fm/ml to 100 pm/ml, after which the LSPR signal saturates. Therefore, we consider 100 fm/ml to 100 pm/ml as the dynamic range of an NM LSPR sensor for this particular embodiment/working example. The LSPR signal change due to absorbed antibody showed less than 3 nm and 0.1 U of change in the LSPR response. These changes are ascribed to non-specific attachment of antibodies at high concentrations on the NM surfaces. We further calculate the limit of detection (NPL 21) of antibody attachment on patterned NMs, which was found to be 65 zM. These results confirm that the NMs can be used as a highly sensitive platform for generic bioassay applications and for the detection of biomolecule binding events on patterned surfaces.

<Additional Details in the Manufacture and Evaluation Experiments Described Above>

Additional details of the manufacture and evaluation experiments described above are provided below, some of which may overlap with the information provided above.

<Nanomushroom Fabrication>

Nanolayers of Au were deposited on both $SiO_2$ and Si substrates using Kawasaki Science KE604TT1-TKF1 electron beam vapor deposition equipment in a class 1000 clean room. The substrates were cleaned with acetone and isopropanol before deposition. A 4 nm Au film was deposited at a rate of 0.3 nm/sec. The sample was then annealed at 560° C. for 3 hours, generating a distribution of Au NIs across the surface of the substrate. Oxford Instruments Plasmalab 100 Inductively Coupled Plasma Chemical Vapor Deposition (ICP CVD) equipment was then used to perform reactive ion etching (RIE) on the sample and generate NMs. $SF_6$ gas was introduced inside the ME chamber, maintained at an inside pressure of 10 mtorr, and a flow rate of 45 sccm (Standard Cubic Centimeters per Minute). The RF power coil and the RF bias coils were fixed to 150 W and 10 W respectively and the temperature inside the plasma chamber was maintained at 5° C.

<Materials Characterization>

Samples were imaged using SEM. A small section of substrate was cut from the original sample using a diamond-tipped glass cutter and attached to a SEM mount using carbon tape. Measurements were taken using an FEI Quanta 250 FEG SEM operating between 5 eV-30 eV to obtain high resolution images with magnification of at least 175 k.

<Measurement of Plasma Effects on Reorganization>

Shields to generate a gradient of reactive ions across the substrate surface during plasma treatment were printed using an Objet 500 3-D printer (Stratasys, Ltd.). The plasma shields were printed using a proprietary polymeric material (Stratasys, Ltd.). These plasma shields had interior dimensions of HEIGHT mm tall, 10 mm wide and 15 mm long. The end of the shield was closed, such that reactive ions could only enter from the front entrance of the shield, thus leading to a unidirectional gradient in reactive ion flux across the substrate. The shield was placed on top of a NI substrate so that the opening to the shield was approximately in the middle of the slide. This placement allowed the use of unshielded parts of the NI surface as a control sample. The shield was held in place using carbon tape to prevent shifting during loading and evacuation of the plasma chamber. After plasma treatment, the shield was removed and the surface was analyzed via SEM as described above.

<Electron Beam Lithography and Characterization of Size Effects on Reorganization>

Electron beam lithography (EBL) was used to fabricate a series of uniformly sized NI arrays. EBL was performed on Si wafers with a thin (10 nm) layer of natural oxide, and on wafers coated in a more robust, 500 nm layer of $SiO_2$. Samples were spin coated with the positive e-beam resist AR-P 6200 at 500 rpm for 10 seconds followed by 6000 rpm for 50 seconds. They were then soft baked at 150° C. for 3 minutes. EBL was performed at 10 pA with a field size of 150, and with the arrays replicated 16 times in a pixel exposure series of 0.8-1.55 s. Development of the EBL patterns was performed for 30 seconds in amyl acetate before being washed in IPA. Large-scale resolution of development was checked with an Olympus BX51 light microscope.

After EBL, electron beam vapor deposition was used to deposit a 10 nm layer of titanium (Ti), followed by a 30 nm layer of Au. Ti was added to increase surface roughness and ensure stronger attachment of Au to the $SiO_2$ surface. Both materials were deposited at a rate of 0.3 nm/sec.

After vapor deposition, lift off was performed by immersing the sample in EBRPG on a hot plate at 50° C. for 20 minutes. A pipette was then used to blow off excess gold without removing the sample from EBRPG. This process left structures only in the arrangement of the EBL pattern. These structures were then imaged in SEM as described above. RIE was performed on these samples to turn the NIs into NMs as described above.

<LSPR Instrumentation and Measurements>

The instrument used to study LSPR response was assembled in laboratory by combining discrete optical components necessary for illumination and collection of light from the sample. The setup is identical to the setups used in our previously published work30, 31. The assembly involves a reflection probe (R400-7UV-VIS), a halogen light source (LS-1-LL) and a spectroscope (USB4000-UV-VIS-ES). Before taking any signal from the spectroscope, the system was calibrated for dark and light spectrum modes. The LSPR signal was then recorded in absorption mode by observing the wavelength dependence of the light absorbed by nanoparticles via the OceanView software (cross-platform spectroscopy operating software from Ocean Optics).

<Cell Proliferation Detection>

The NM substrates were placed into 35 mm (9 cm2) corning cell-culture dishes. The NMs were sterilized using isopropanol, 70% ethanol, and finally allowed to dry in the cell-culture biosafety cabinet under UV light. PDL solution was made at 0.003% in PBS, for a volume of 500 1 per NM substrate. Devices were coated with the PDL solution and placed into the cell-culture incubator, a humidified environment at 37° C. with 5% $CO_2$, for 30 minutes. Dishes were then pre-filled with 1 mL of Dulbecco's Modified Eagle Medium high glucose (DMEM) supplemented with 10% calf serum. NIH/3T3 fibroblasts were then seeded in the dish at low densities (approximately $0.2 \times 10^6$ cells per dish). Cell-culture media was then added to make the final volume 2 mL. An LSPR reading was made immediately. Cells were then allowed to grow in the cell-culture incubator for the indicated amount of time. No new cell-culture medium was added or removed from the dish for the duration of the experiment. For cell-number experiments the Au NM devices were washed with 1xPBS two times after taking an LSPR measurement. After this, 1 mL of trypsin was added to strip cells. The number of cells were counted using a hematocytometer.

<Microcontact Printing and Bioassay>

Stamps designs comprising of (i) an array of 50 mx50 m squares with 50 m spacing (ii) the logo of the university (50 m thickness with a total diameter of 1 mm), were designed with AutoCAD (AutoDesk, USA). For fabricating the master for the stamps, silicon wafers (4-inch in diameter, EM Corp. Ltd., Japan) were coated with a 50 m layer of mr-DWL 40 photoresist (Microresist technologies, Germany), and the features were patterned by photolithography using a DL1000 maskless writer (NanoSystem Solutions, Japan) and developed using mr-Dev 600 developer (Microresist Technologies, Germany). After thorough baking and cleaning, the wafers were coated with an anti adhesive layer by exposing it to trichloro(1H, 1H, 2H 2H-perfluorooctyl) silane (Sigma-Aldrich, Japan) in vapor phase in a desiccator. PDMS stamps with the inverse copy of the pattern present on the Si-wafer were obtained by pouring 10:1 poly-(dimethylsiloxane) (PDMS) (DOW Corning, Japan) on the wafer and curing the pre-polymer for 24 h at 60° C. after degassing to remove air bubbles.

Prior to the microcontact printing process, the NI and NM substrates were cleaned with ethanol and dried well. The patterned stamps were inked with 10 L of Alexa Fluor 546 conjugated goat anti-chicken Immunoglobulins (IgGs) (Abcam, Japan) at a concentration of 10 g/ml in 1xPBS, for 5-7 min under a plasma activated (Harrick Plasma, USA) coverslip. The stamps were rinsed with 1xPBS followed by milli-Q water (Millipore, Japan) for 5 s each before rapid drying with a strong pulse of $N_2$ gas. The inked PDMS stamps were then contacted with pre-cleaned substrates for 5 s. Subsequently, the micropatterns of the fluorescently labeled IgGs were imaged on a Ti-E Eclipse inverted fluorescent microscope (Nikon, Japan) with a fixed exposure time of 10 s for all samples. After confirming the presence of printed primary antibody, the patterned antibodies were exposed to varied concentrations of secondary antibody for dose-response bioassay studies.

Portable LSPR Device

As an additional embodiment of the present invention, a portable LSPR device is described below. FIG. 19 shows the main components of the manufactured LSPR sensor device. As shown in FIG. 19, the device includes 5 parts: A) a LED based light source panel, B) the LSPR chip of the present invention, C) fluidic Stage, D) Spectrometer Panel, and E) Readout component. These components are put together, forming a device that measures nanoplasmonic resonances from the nanomushrooms (NM) LSPR chip. The disclosed device design is particularly useful when incorporated with the nanomushroom LSPR chip of the present invention due to the high sensitivity of the LSPR chip, but the device may use more generic LSPR chips having similar dimensions.

The light source of this embodiment includes a white light emitting diode. The circuit diagram of the circuit for the LED is shown in FIG. 20. As shown in FIG. 20, the circuit is made up of 6 components 1. LED, 2. Voltage booster, 3. Battery pack, 4. Solar cell, 5. Diode with low reverse bias, and 6. Switch. This way, electric power from the solar cell and/or the battery pack can be used to energize the LED so that the LED emits light.

FIGS. 21-23 are various views of the light source panel included in the present embodiment, including several side views, top and bottom views, and front and back views. As shown in these figures. A solar panel is attached on the top, and a LED is provided at the bottom facing downwardly. A reflector is provide surrounding the LED. A PCB is provided adjacent to the LED. A switch is provided at the back of the panel. The PCB includes various additional electronic components, such as a variable resistor to control intensity of light, a touch screen was also provided to control the light intensity.

The NM chip described above was used as the LSPR chip incorporated in this portable LSPR device.

In this embodiment. C12666MA and C12880MA spectrometers made by Hamamatsu were used for capturing the spectral response of the LSPR chip. These spectrometers are controlled using Arduino board to acquire LSPR response. Block diagram describing the logic, electronics and connection within various components is described in FIG. 24.

The various parts of the spectrometer are described below:

1) Power Supply: One power bank supplies energy required to power complete spectrometer module consisting of microcontroller, display and the microspectrometer. Power supply of 5 V is necessary for the spectrometer. This potential of 5 V is provided by means of a rechargeable battery powered either by a solar panel or by direct power supply.

2) Microcontroller: This is the main control unit of the spectrometer. There are important 3 tasks performed by the microcontroller. First it provides clock signals to the spectrometer (input to spectrometer) for controlling the duration for which spectrometer is exposed to light. This duration is also known as the integration time of spectrometer. Secondly, the microcontroller communicates with spectrometer and receives signals acquired by spectrometer during integration time (output of spectrometer). Finally, the microcontroller communicates with the display unit or graphics user interface to display the acquired spectrum.

The Fluidic Stage of the portable LSPR device of the present embodiment is constructed as follows. The device has a fluidic channel that allows fluid to pass over the plasmonic chips. The fluidic channels are made up of acrylic material. It is transparent and allows light to reach the nanostructures on the LSPR chips. FIGS. 25(a) to 25(c) show the design drawings of the Fluid Stage: FIG. 25(a) shows a bird view of fluidic channel; FIG. 25(b) shows a side view of the fluidic channel integrated in LSPR system and its magnified view; and FIG. 26(c) shows the top and the cross-sectional views of the fluidic channel. The arrows indicate the direction of fluid in the channel.

The fluidic channel consists of an O-ring which forms air tight connections with plasmonic chip to avoid fluidic leakage. For example, the size (5 mm long) and shape (circular, 1.2 mm in diameter) of channels can be costumed ranging from 10 micron to 10 mm, see FIG. 25. The fluidic channel was held in contact with plasmonic chip using the donut-shaped pressurizer which can be attached in the holder using a detachable key. FIG. 26(a) schematically shows the stage holder attached to the light source panel, FIG. 26(b) schematically shows the donut shaped pressurizer, and FIG. 26(c) schematically shows a detachable key for attaching pressurizer on the stage. All major mechanical structures are designed with concentric holes for aligning optical path using a 3D printer.

FIG. 27 shows a flowchart of all steps involved in readout and displaying the signals from the spectrometer according to the present embodiment. There are three aim tasks of the readout. The first task is initialization of the software which involves serial communication with microcontroller to acquire precise wavelength vibration parameters. After initialization, the software acquires background and reference signals which are later processed to display absorbance of the signal.

FIG. 28 shows a graphics user interface developed in Matlab to display the LSPR signal in real time. The panel consists of a panel which allows user to change the interrogation time, fix the time of acquisition and then follow the kinetics of the measurement by observing wavelength and absorbance shifts in plasmonic resonances. The readout is also integrated with touch screen display panel.

As escribed above, as an embodiment of the present invention, a portable and highly effective LSPR device was made utilizing the LSPR chip of the present invention. Due to the high sensitive and effective nature of the LSPR chip and structure of the present disclosure, the resulting LSPR device was also very effective and reliable.

It will be apparent to those skilled in the art that various modifications and variations can be made in the present invention without departing from the spirit or scope of the invention. Thus, it is intended that the present invention cover modifications and variations that come within the scope of the appended claims and their equivalents. In particular, it is explicitly contemplated that any part or whole of any two or more of the embodiments and their modifications described above can be combined and regarded within the scope of the present invention.

The invention claimed is:

1. A method for making a plasmonic mushroom array, comprising:
   depositing a layer of metal on the surface of the glass substrate; and
   forming a plurality of metal nano-islands on the surface of the glass substrate by either (i) annealing the glass substrate having the layer of metal formed thereon to cause dewetting of the metal to occur, or (ii) patterning the layer of metal by photolithography, so as to form the plurality of metal nano-islands on the surface of the glass substrate at a spacing of 100 nm or less between adjacent metal nano-islands, each of the plurality of metal nano-islands having nanometer-range dimensions, and
   subjecting to the glass substrate having the plurality of metal nano-islands formed thereon to reactive ion etching to form a first plurality of mushroom-shaped structures at positions of the plurality of metal nano-islands and a second plurality of mushroom-shaped structures within the spacing between the first plurality of mushroom-shaped structures,
   wherein each of the first plurality of mushroom-shaped structures and the second plurality of mushroom-shaped structures has a metal cap supported by a pillar made of a material of the glass substrate and each of the first plurality of mushroom-shaped structures and the second plurality of mushroom-shaped structures has dimensions smaller than the dimensions of the nano-islands,
   wherein the first plurality of mushroom-shaped structures and the second plurality of mushroom-shaped structures are arranged in a substantially regular pattern with intervals smaller than average intervals between the nano-islands,
   thereby forming the plasmonic mushroom array on the glass substrate that can exhibit localized surface plasmon resonance.

2. The method according to claim 1,
   wherein the metal is gold, a thickness of the layer of metal is 4 nm, the glass substrate is an $SiO_2$ substrate, and the annealing is conducted at a temperature of 560° C. for 3 hours, and
   wherein the reactive ion etching is performed with a gas of $SF_6$ at 5° C.

3. The method according to claim 1,
   wherein the forming of the plurality of metal nano-islands is performed such that the plurality of metal nano-islands each have a diameter of 100 nm or less.

4. The method according to claim 1,
   wherein the metal is gold, and the glass substrate is an $SiO_2$ substrate,
   wherein the forming of the plurality of metal nano-islands is performed such that the plurality of metal nano-islands each have a metal island made of gold having a diameter of 5 nm-70 nm and a height of 20 nm-25 nm with a spacing between the nano-islands being 2 nm-80 nm, and
   wherein the reactive ion etching is performed such that the resulting plurality of mushroom-shaped structures each have the metal cap made of gold with a diameter of 10 nm-30 nm and a height of 15 nm-20 nm, supported by the pillar made of $SiO_2$ having a height of 30 nm-40 nm, with a spacing between the mushroom-shaped structures being 5 nm to 20 nm.

5. The method according to claim 1,
   wherein the metal is gold, and the glass substrate is an $SiO_2$ substrate,
   wherein the forming of the plurality of metal nano-islands is performed such that the plurality of metal nano-islands each have a metal island made of gold having an average diameter of 35 nm and a height of 20 nm-25 nm with an average spacing between the nano-islands being 25 nm, and wherein the reactive ion etching is performed such that the resulting plurality of mushroom-shaped structures each have the metal cap made of gold with an average diameter of 25 nm and a height of 15 nm-20 nm, supported by the pillar made of $SiO_2$ having a height of 30 nm-40 nm, with an average spacing between the mushroom-shaped structures being 10 nm.

6. The method according to claim 1, wherein the reactive ion etching causes a metal of the metal nano-islands to be redistributed and etched on the surface of the glass substrate, so as to form the second plurality of mushroom-shaped structures.

7. The method according to claim 1, wherein the plurality of metal nano-islands are heterogeneously distributed on the surface of the glass substrate, and wherein the first and second pluralities of mushroom-shaped structures are homogeneously distributed on the surface of the glass substrate.

8. A plasmonic plate, comprising:

a glass substrate;

a first plurality of mushroom-shaped structures on the glass substrate with a spacing therebetween, and a second plurality of mushroom-shaped structures within the spacing between the first plurality of mushroom-shaped structures, wherein each of the first plurality of mushroom-shaped structures and the second plurality of mushroom-shaped structures has a metal cap supported by a pillar made of a material of the glass substrate and each has nano-scale dimensions, wherein metal caps of the second plurality of mushroom-shaped structure are formed of metal redistributed from metal caps of the first plurality of mushroom-shaped structure, and wherein the first plurality of mushroom-shaped structures and the second plurality of mushroom-shaped structures are arranged in a substantially regular pattern so as to exhibit localized surface plasmon resonance.

9. The plasmonic plate according to claim 8, wherein the glass substrate is an $SiO_2$ substrate, and wherein the first plurality of mushroom-shaped structures and the second plurality of mushroom-shaped structures each have the metal cap made of gold with a diameter of 10 nm-30 nm and a height of 15 nm-20 nm, supported by the pillar made of $SiO_2$ having a height of 30 nm-40 nm, with a spacing between adjacent mushroom-shaped structures being 5 nm to 20 nm.

10. A plasmonic chip, comprising a plurality of plasmonic areas, each of the plasmonic areas being the plasmonic plate set forth in claim 9.

11. A localized surface plasmon resonance device, comprising:

an LED circuit including a light emitting diode emitting light downwardly;

a plasmonic chip disposed under the LED circuit, the plasmonic chip including the plasmonic plate as set forth in claim 9, and facing the light emitting diode to receive light from the light emitting diode;

a fluid stage disposed under the LED circuit such that a fluid provided in the fluid stage can operably couple with the plasmonic plate; and a spectrometer disposed under the plasmonic chip to receive light that has interacted with the plasmonic plate so as to analyze spectrum of the received light.

12. The plasmonic plate according to claim 8, wherein the glass substrate is an $SiO_2$ substrate, and wherein the first plurality of mushroom-shaped structures and the second plurality of mushroom-shaped structures each have the metal cap made of gold with an average diameter of 25 nm and a height of 15 nm-20 nm, supported by the pillar made of $SiO_2$ having a height of 30 nm-40 nm, with an average spacing between adjacent mushroom-shaped structures being 10 nm.

13. A plasmonic chip, comprising a plurality of plasmonic areas, each of the plasmonic areas being the plasmonic plate set forth in claim 12.

14. A localized surface plasmon resonance device, comprising:

an LED circuit including a light emitting diode emitting light downwardly;

a plasmonic chip disposed under the LED circuit, the plasmonic chip including the plasmonic plate as set forth in claim 12, and facing the light emitting diode to receive light from the light emitting diode;

a fluid stage disposed under the LED circuit such that a fluid provided in the fluid stage can operably couple with the plasmonic plate; and a spectrometer disposed under the plasmonic chip to receive light that has interacted with the plasmonic plate so as to analyze spectrum of the received light.

15. A plasmonic chip, comprising a plurality of plasmonic areas, each of the plasmonic areas being the plasmonic plate set forth in claim 8.

16. A localized surface plasmon resonance device, comprising:

an LED circuit including a light emitting diode emitting light downwardly;

a plasmonic chip disposed under the LED circuit, the plasmonic chip including the plasmonic plate as set forth in claim 8, and facing the light emitting diode to receive light from the light emitting diode;

a fluid stage disposed under the LED circuit such that a fluid provided in the fluid stage can operably couple with the plasmonic plate; and a spectrometer disposed under the plasmonic chip to receive light that has interacted with the plasmonic plate so as to analyze spectrum of the received light.

\* \* \* \* \*